(12) United States Patent
O'Hara et al.

(10) Patent No.: US 11,173,170 B2
(45) Date of Patent: *Nov. 16, 2021

(54) PREBIOTIC COMPOSITION AND ITS METHODS OF PRODUCTION

(71) Applicant: Optibiotix Limited, Yorkshire (GB)

(72) Inventors: Stephen Patrick O'Hara, Yorkshire (GB); Sofia Kolida, Yorkshire (GB)

(73) Assignee: Optibiotix Limited, Yorkshire (GB)

( * ) Notice: Subject to any disclaimer, the term of this patent is extended or adjusted under 35 U.S.C. 154(b) by 72 days.

This patent is subject to a terminal disclaimer.

(21) Appl. No.: 15/523,704

(22) PCT Filed: Nov. 5, 2015

(86) PCT No.: PCT/GB2015/053349
§ 371 (c)(1),
(2) Date: May 2, 2017

(87) PCT Pub. No.: WO2016/071692
PCT Pub. Date: May 12, 2016

(65) Prior Publication Data
US 2018/0303857 A1  Oct. 25, 2018

(30) Foreign Application Priority Data

Nov. 5, 2014 (WO) ............... PCT/GB2014/053303
May 5, 2015 (GB) ................................... 1507664

(51) Int. Cl.
*A61K 31/702* (2006.01)
*A23L 33/21* (2016.01)
*A23L 2/52* (2006.01)
*A61K 35/747* (2015.01)
*A61K 45/06* (2006.01)
*A61K 35/741* (2015.01)
*A23L 29/269* (2016.01)
*A23L 33/135* (2016.01)
*A23L 33/26* (2016.01)
*A61K 9/00* (2006.01)
*A61K 9/50* (2006.01)
*A61K 49/00* (2006.01)
*C12Q 1/02* (2006.01)
*A23L 33/00* (2016.01)
*A61P 3/04* (2006.01)
*A61P 3/06* (2006.01)
*A61P 3/10* (2006.01)
*A61K 31/715* (2006.01)

(52) U.S. Cl.
CPC .............. *A61K 31/702* (2013.01); *A23L 2/52* (2013.01); *A23L 29/269* (2016.08); *A23L 33/135* (2016.08); *A23L 33/21* (2016.08); *A23L 33/26* (2016.08); *A23L 33/30* (2016.08); *A61K 9/0053* (2013.01); *A61K 9/50* (2013.01); *A61K 31/715* (2013.01); *A61K 35/741* (2013.01); *A61K 35/747* (2013.01); *A61K 45/06* (2013.01); *A61K 49/0004* (2013.01); *A61P 3/04* (2018.01); *A61P 3/06* (2018.01); *A61P 3/10* (2018.01); *C12Q 1/025* (2013.01); *A23V 2002/00* (2013.01); *A23V 2200/00* (2013.01); *A23V 2200/3202* (2013.01); *A23V 2200/328* (2013.01); *A23V 2200/3262* (2013.01); *A23V 2200/332* (2013.01); *A23Y 2220/00* (2013.01); *A23Y 2220/35* (2013.01); *A23Y 2220/71* (2013.01); *G01N 2333/335* (2013.01); *G01N 2333/938* (2013.01); *G01N 2500/10* (2013.01)

(58) Field of Classification Search
CPC ......... A23L 29/269; A23L 33/30; A23L 33/26
See application file for complete search history.

(56) References Cited

U.S. PATENT DOCUMENTS

| 7,794,746 B2 * | 9/2010 | Gibson ................. A23C 9/203 424/439 |
| 9,913,857 B2 * | 3/2018 | O'Hara ................. A23L 33/135 |
| 2008/0254011 A1 | 10/2008 | Rothschild et al. |
| 2011/0254011 A1 | 10/2011 | Kim et al. |
| 2012/0171165 A1 * | 7/2012 | Buck .................... A61K 31/702 514/23 |
| 2012/0213753 A1 | 8/2012 | Cune Castellana |
| 2014/0072544 A1 | 3/2014 | Dimitrov et al. |

FOREIGN PATENT DOCUMENTS

| EP | 2163162 A1 | 3/2010 |
| WO | 2010124387 A1 | 11/2010 |
| WO | 2016071692 A1 | 5/2016 |

OTHER PUBLICATIONS

Iqbal (Carbohydrate Research; 345, 2010, 1408-1416).*
Fabrizio (Journal of Clinical Gastroenterology; vol. 42, Supp.3, Part 2, 2008; S224-S233).*
Gobinath et al., "Permeabilized probiotic Lactobacillus plantarum as a source of B-galactosidase for the synthesis of prebiotic galactooligosaccharides", "Biotechnol Lett", Sep. 28, 2013, pp. 153-157, vol. 36, Publisher: Springer Science+Business Media Dordrecht.

(Continued)

*Primary Examiner* — Pancham Bakshi
(74) *Attorney, Agent, or Firm* — Fredrikson & Byron, P.A.; Sean Solberg

(57) ABSTRACT

The present invention relates to a prebiotic composition comprising a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse β-galactosidase reaction in the chosen probiotic bacterial strain. The present invention also relates to methods of producing GOS and related composition incorporating the GOS.

7 Claims, 27 Drawing Sheets

(56) References Cited

OTHER PUBLICATIONS

Pereira et al., "An In Vitro Study of the Probotic Potential of a Bile-Salt-Hydrolyzing Lactobacillus fermentum Strain, and Determination of Its Cholesterol-lowering Properties", "Applied and Environmental Microbiology", Aug. 2003, pp. 4743-4752, vol. 69, No. 8, Publisher: American Society for Microbiology, Published in: US.

Rabiu et al., "Synthesis and Fermentation Properties of Novel Galacto-Oligosaccharides by B-Galactosidases from *Bifidobacterium* Species", "Applied and Environmental Microbiology", Jun. 2011, pp. 2526-2530, vol. 67, No. 6, Publisher: American Society for Microbiology, Published in: US.

Splechtna et al., "Production of Prebiolic Ga!acto-O!igosaccharides from Lactose Using B-Galactosklases from Lactobacillus reuteri", Jun. 21, 2006, pp. 4999-5006, vol. 54, No. 14, Publisher: Journal of Agricultural and Food Chemistry.

Tzortzis et al., "In Vito evaluation of th fermentation properties of galactooligosaccharides synthesised by a-galactosidase from Lactobacillus reuteri", "Appl Microbiol Biotechnol", Sep. 6, 2003, pp. 106-111, vol. 64, Publisher: Springer-Verlag.

\* cited by examiner

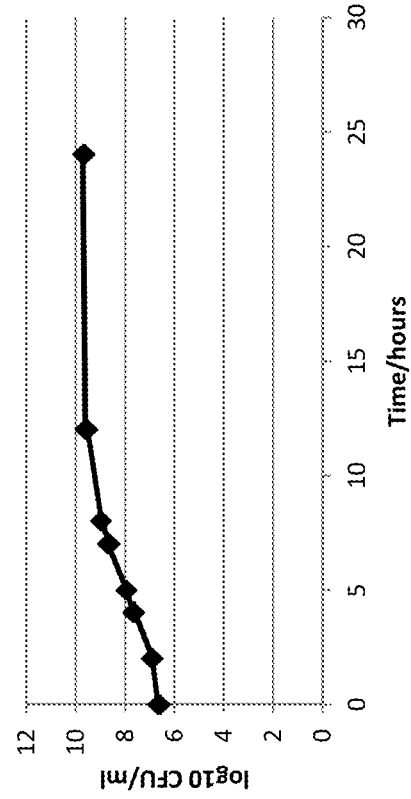
Figure 1A L. plantarum
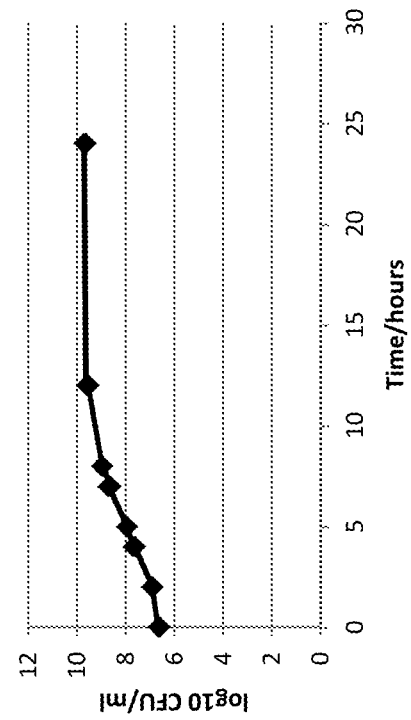
Figure 1C L. salivarius
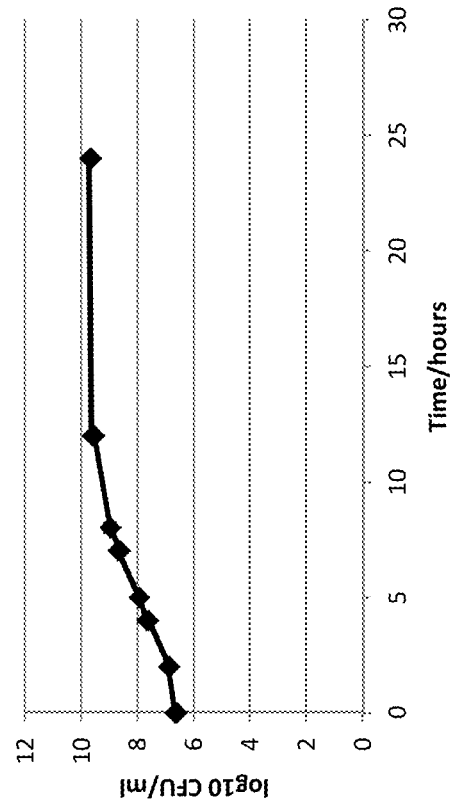
Figure 1B L. casei
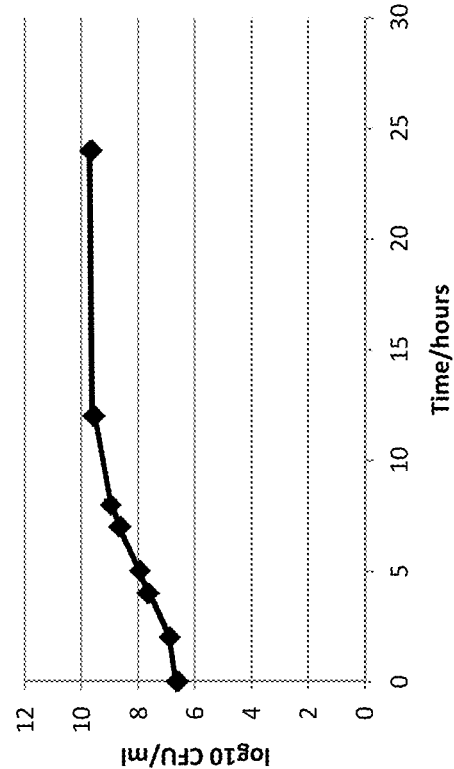
Figure 1D L. fermentum

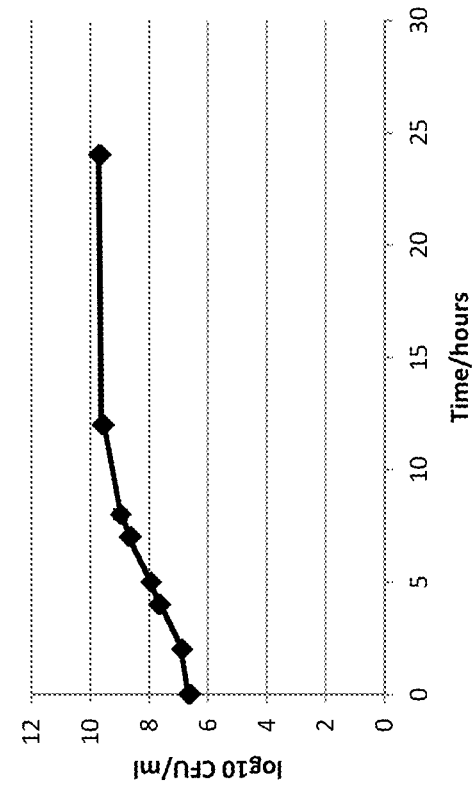
Figure 1F  L. delbrueckii
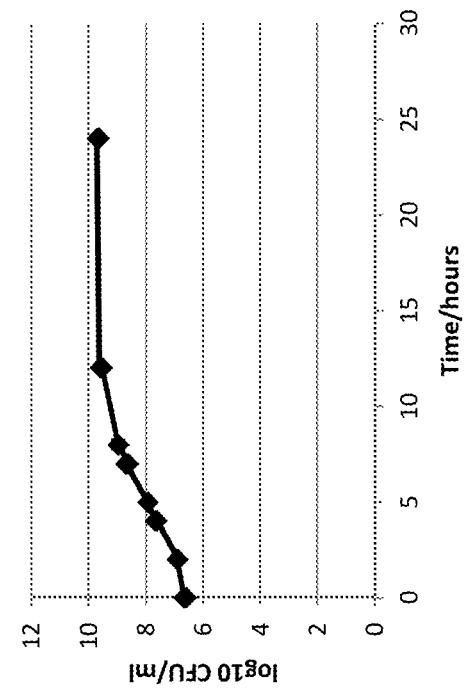
Figure 1E  L. rhamnosus

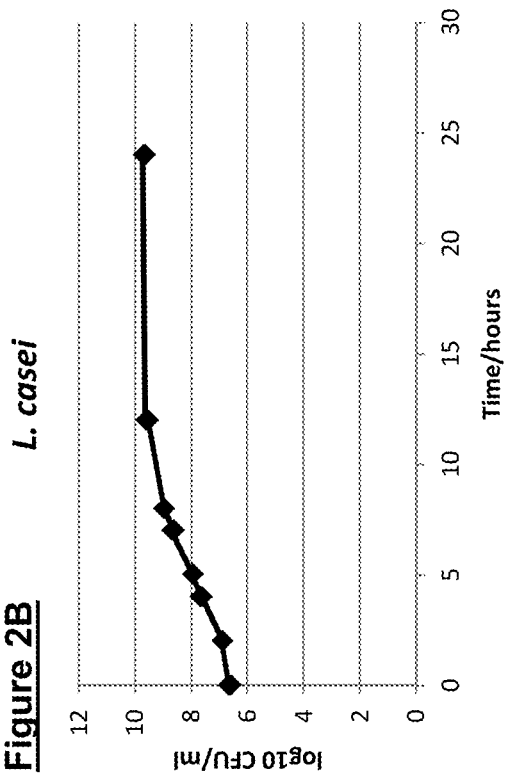
Figure 2A   L. plantarum
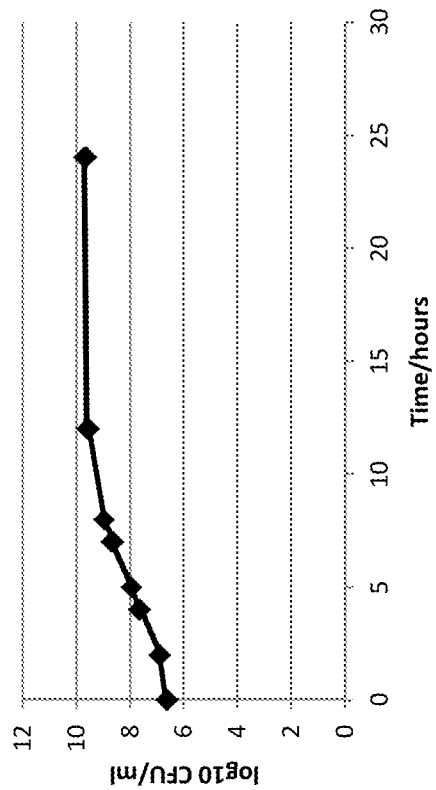
Figure 2B   L. casei
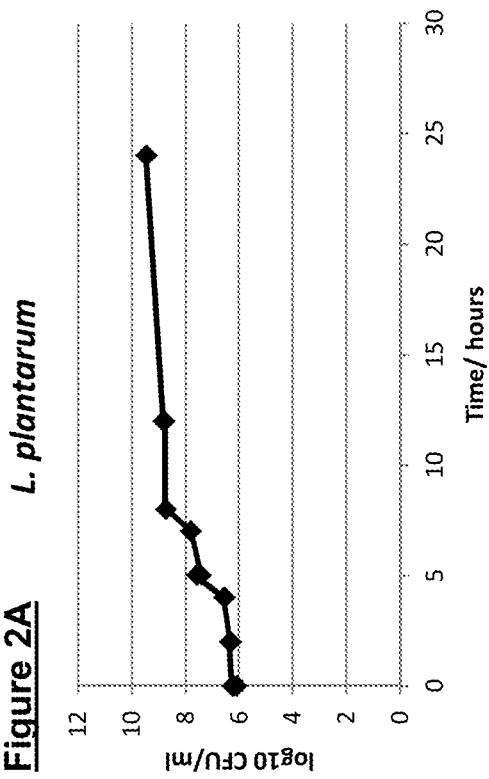
Figure 2C   L. salivarius
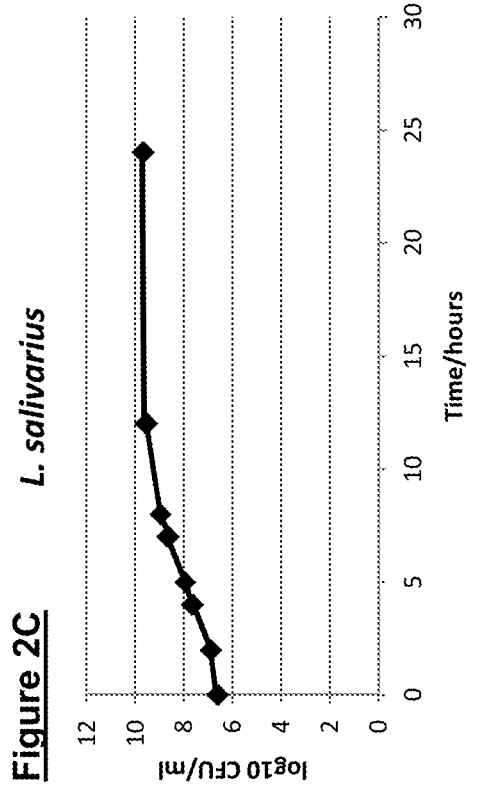
Figure 2D   L. delbrueckii

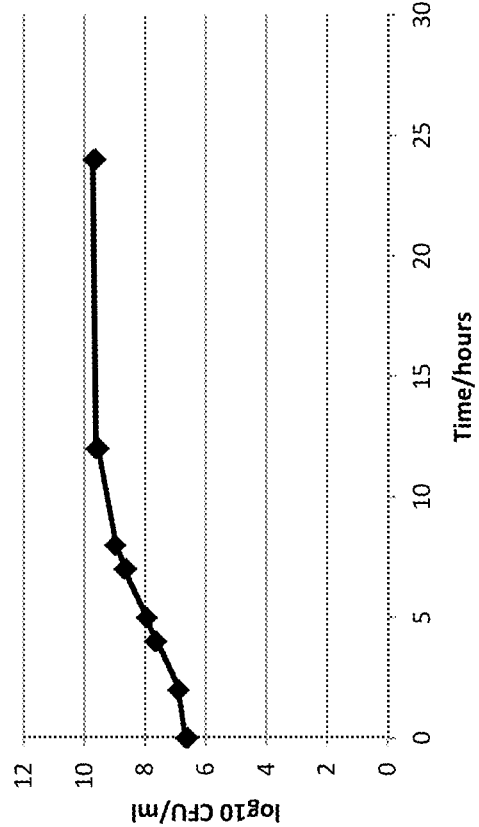
Figure 2E *L. rhamnosus*
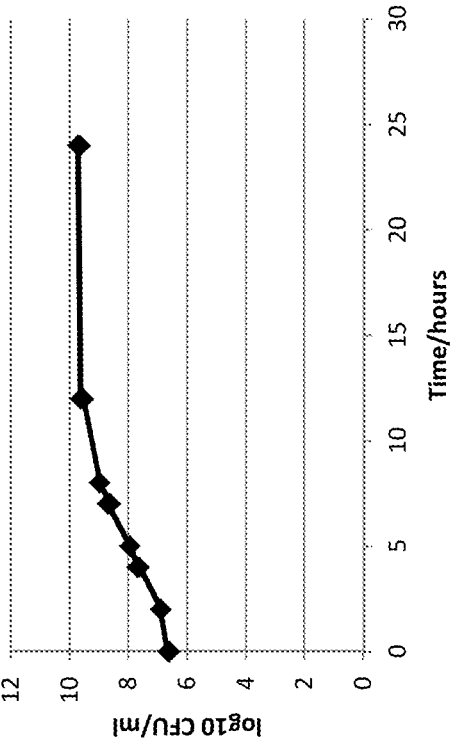
Figure 2F *L. acidophilus*
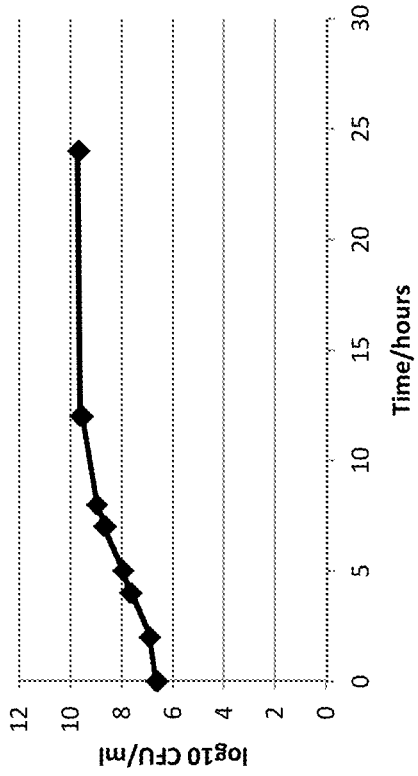
Figure 2G *L. helveticus*

Figure 9
Sugars
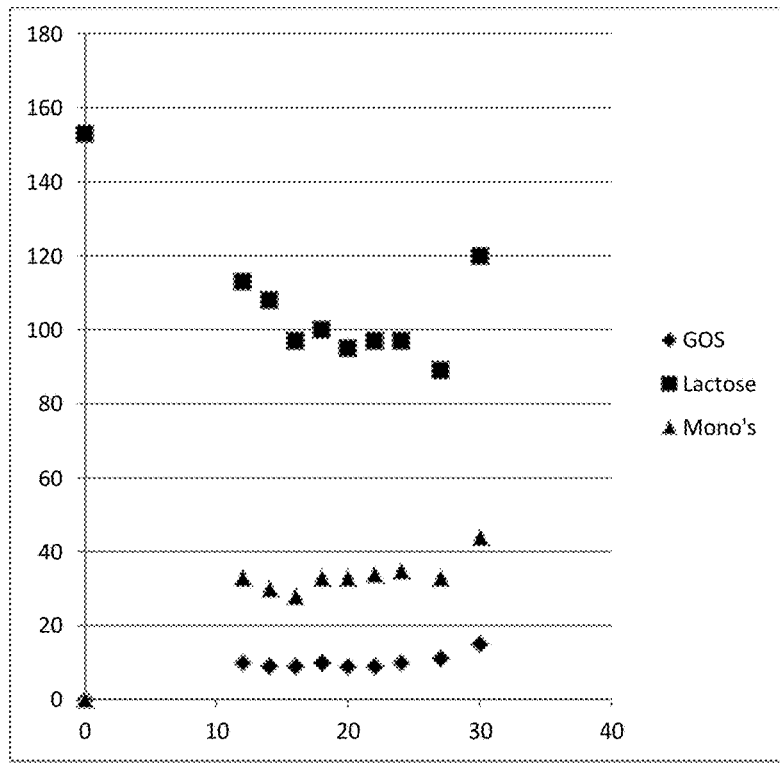
GOS%
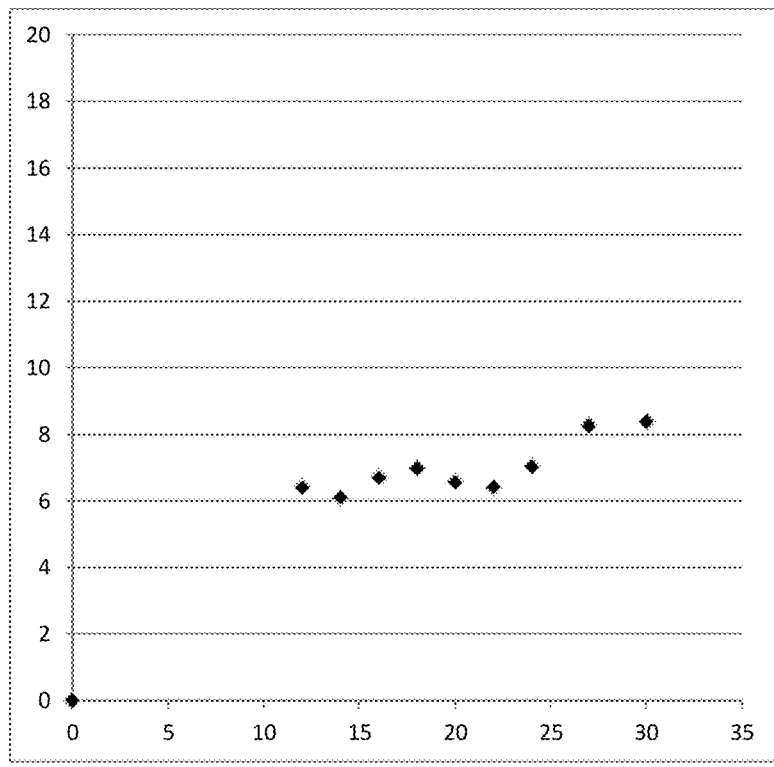

Figure 10
Sugars
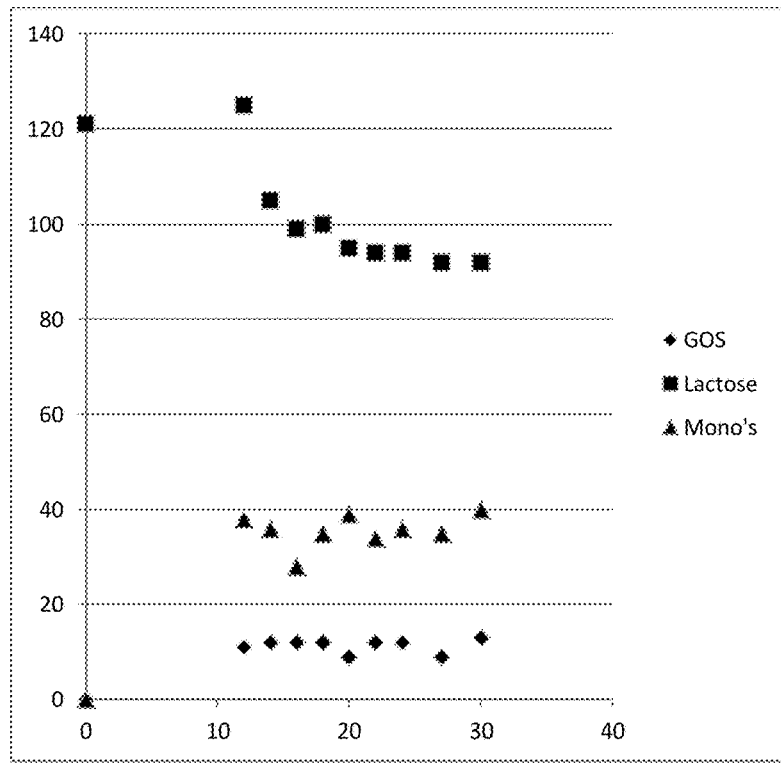
GOS%
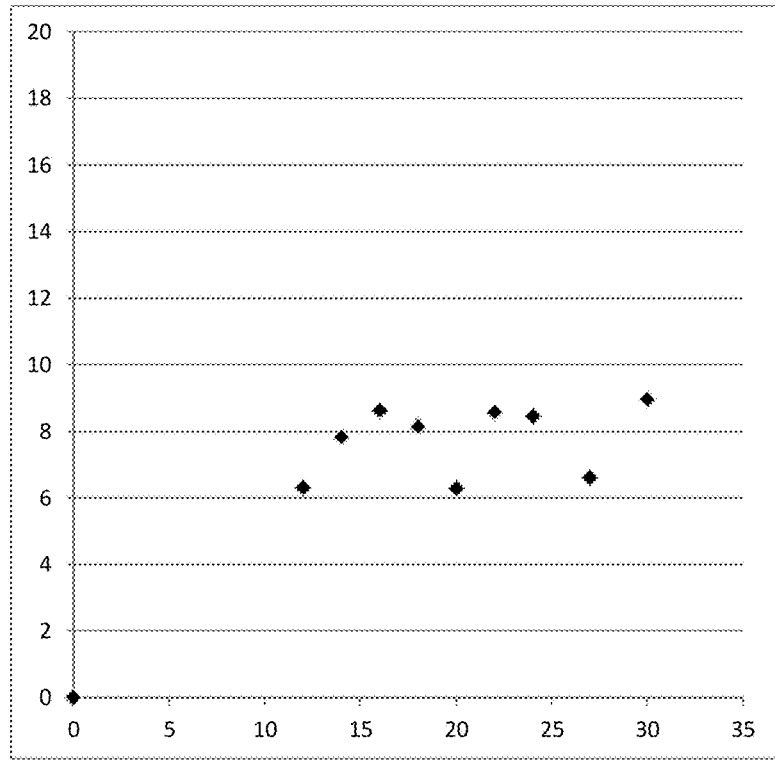

Figure 11
Sugars
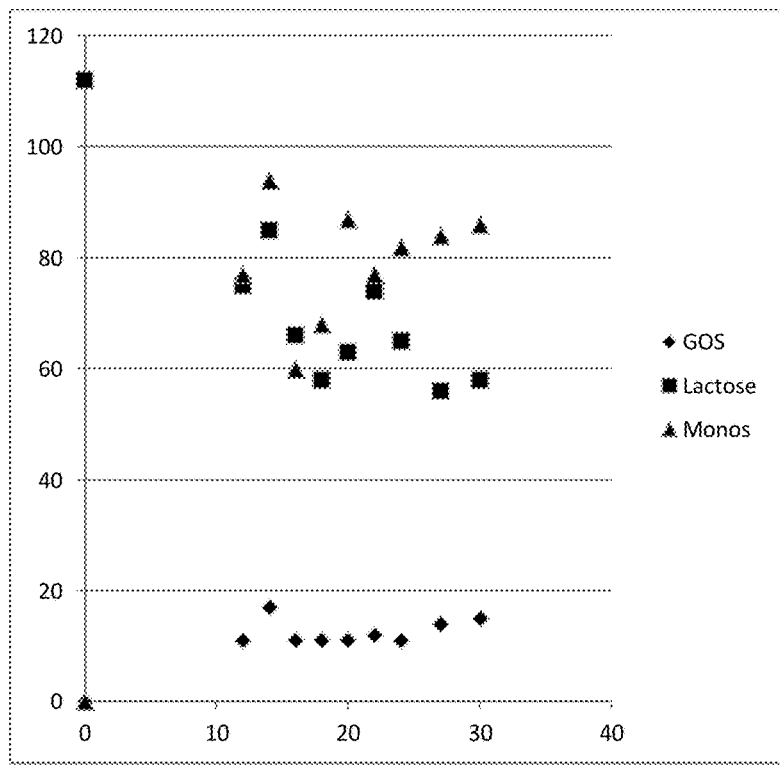
GOS%
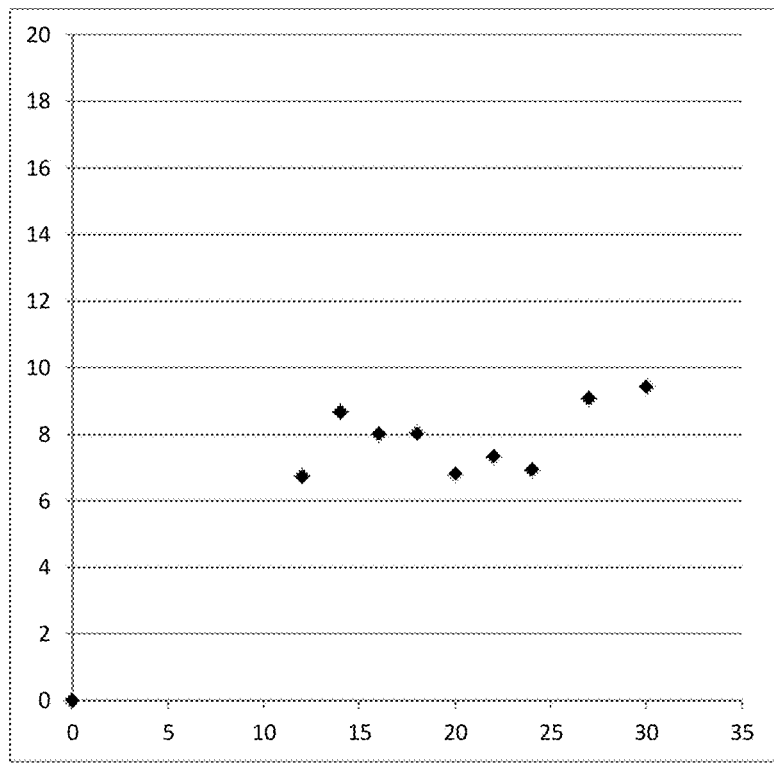

Figure 12
Sugars
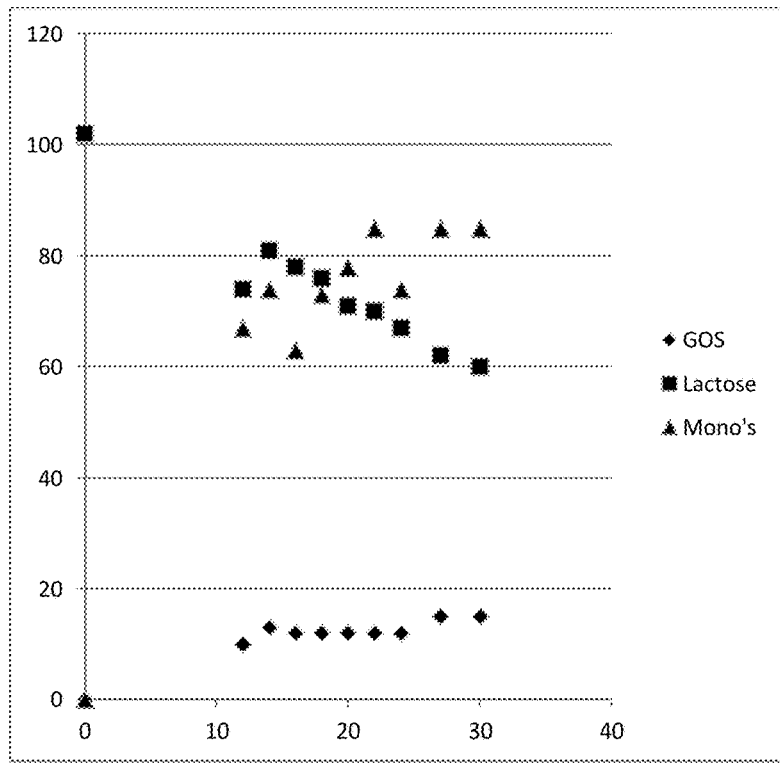
GOS%
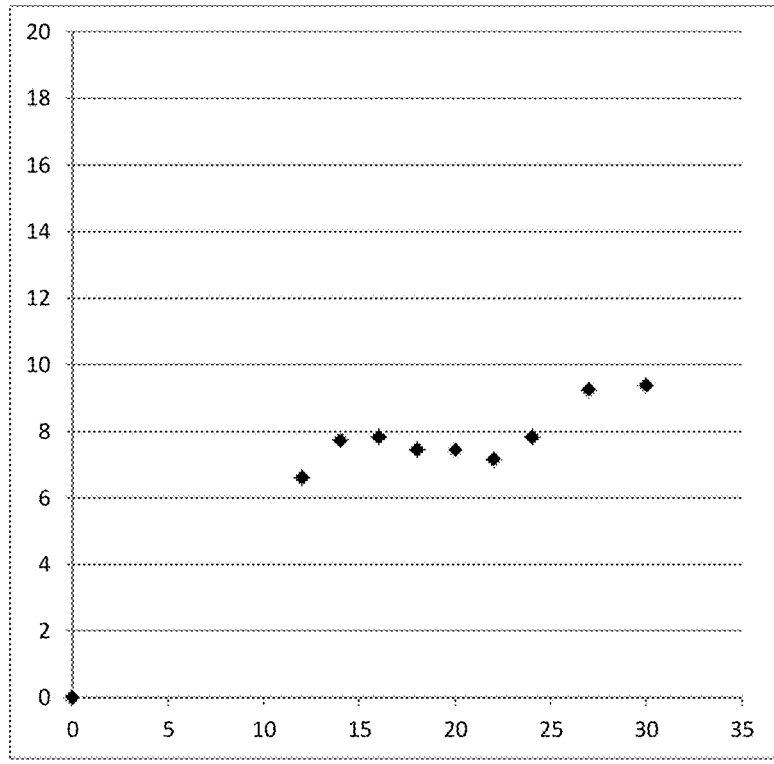

Figure 13
Sugars
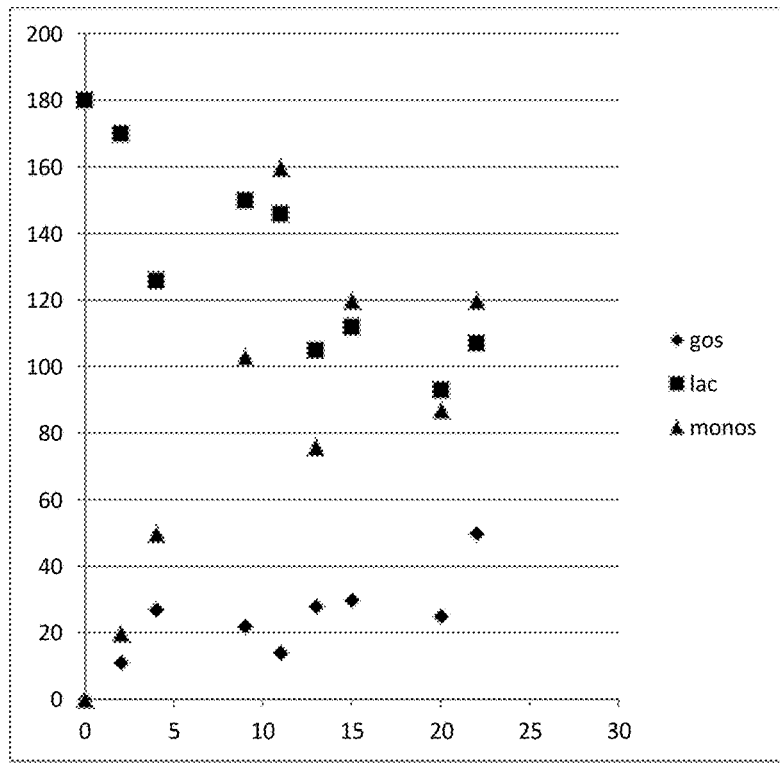
GOS%
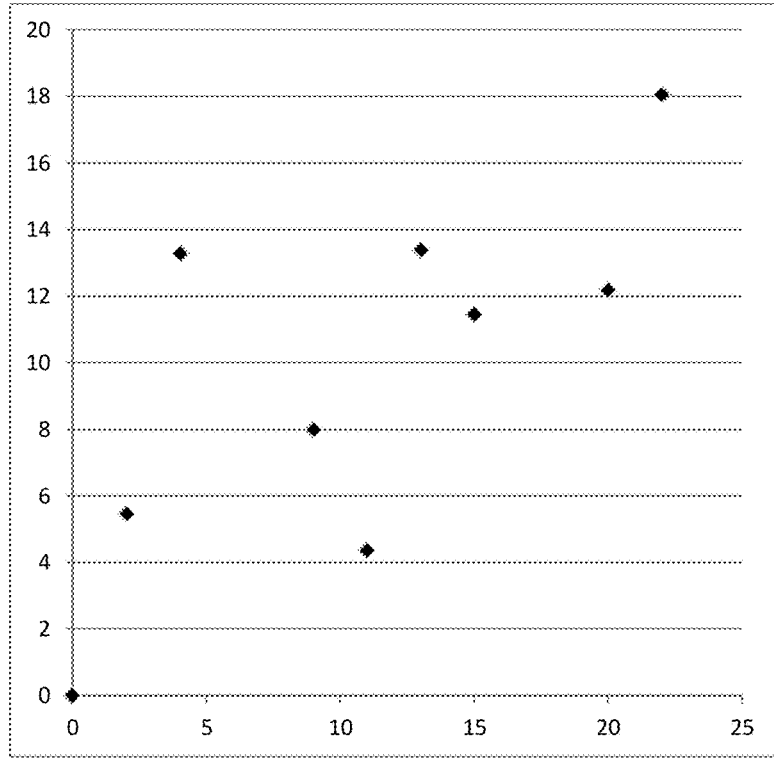

Figure 14
Sugars
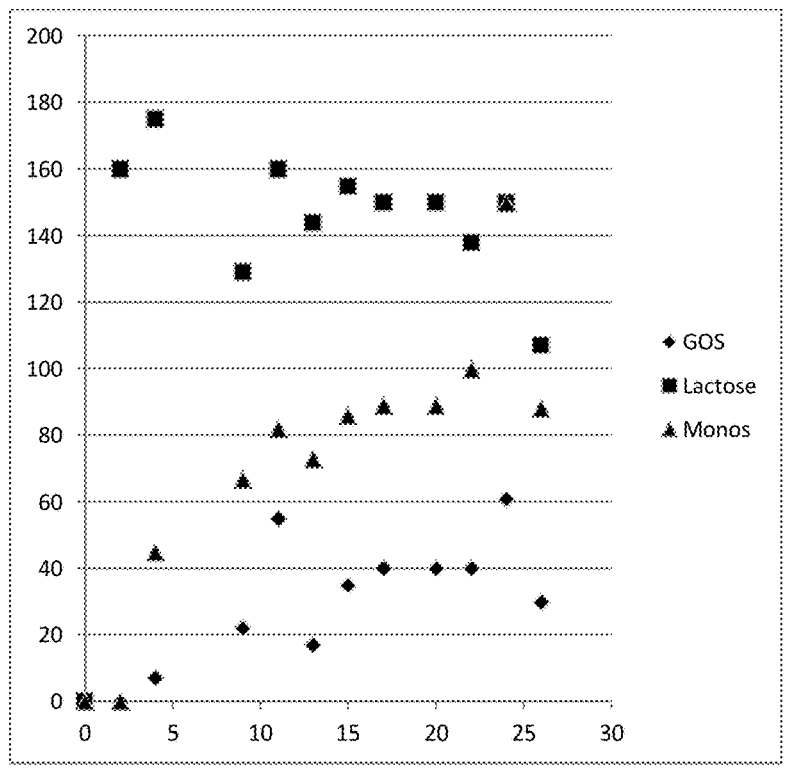
GOS %
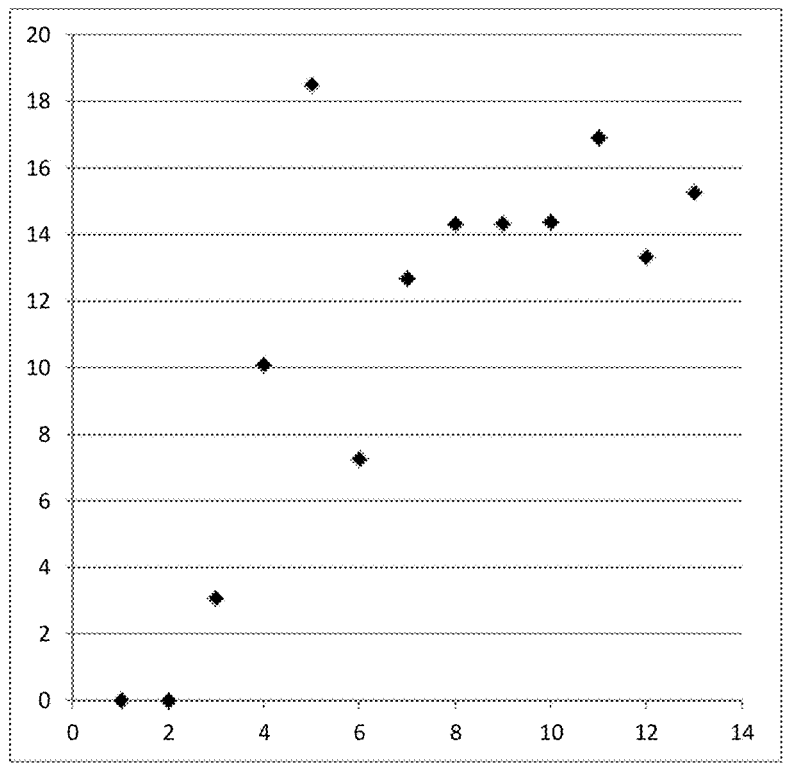

Figure 15
Sugars
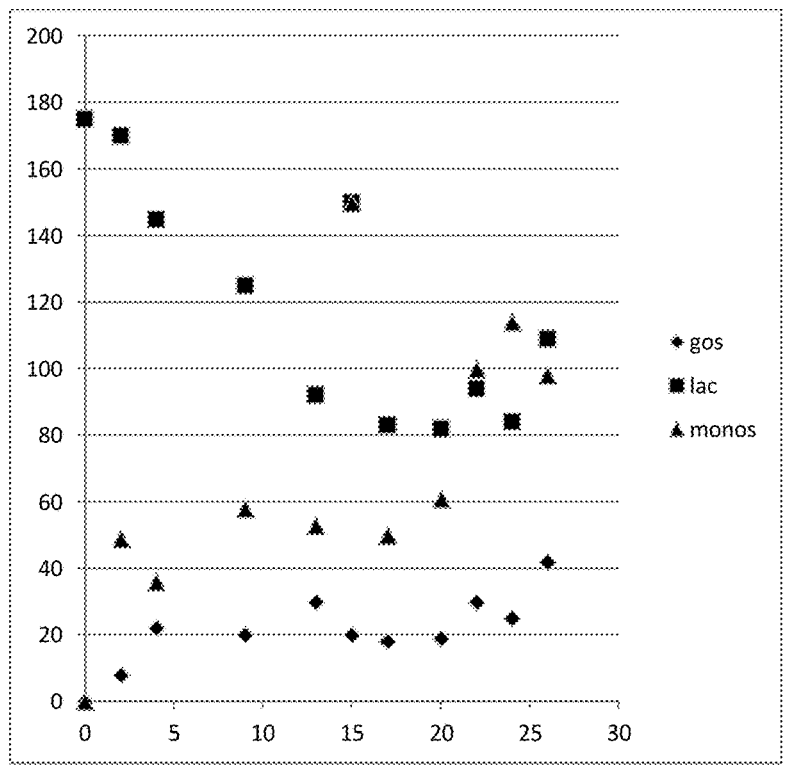
GOS%
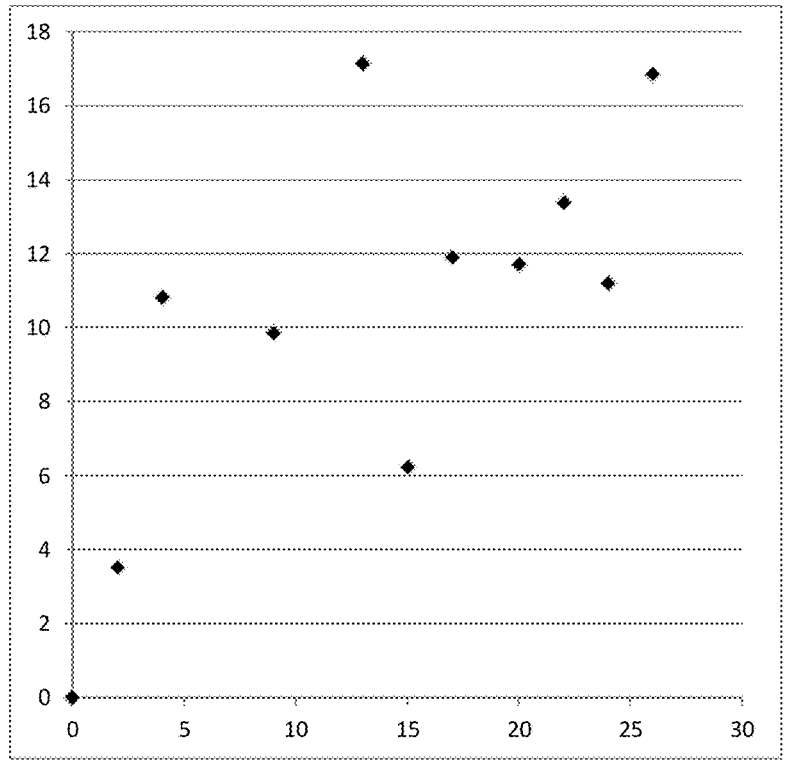

Figure 16
Sugars
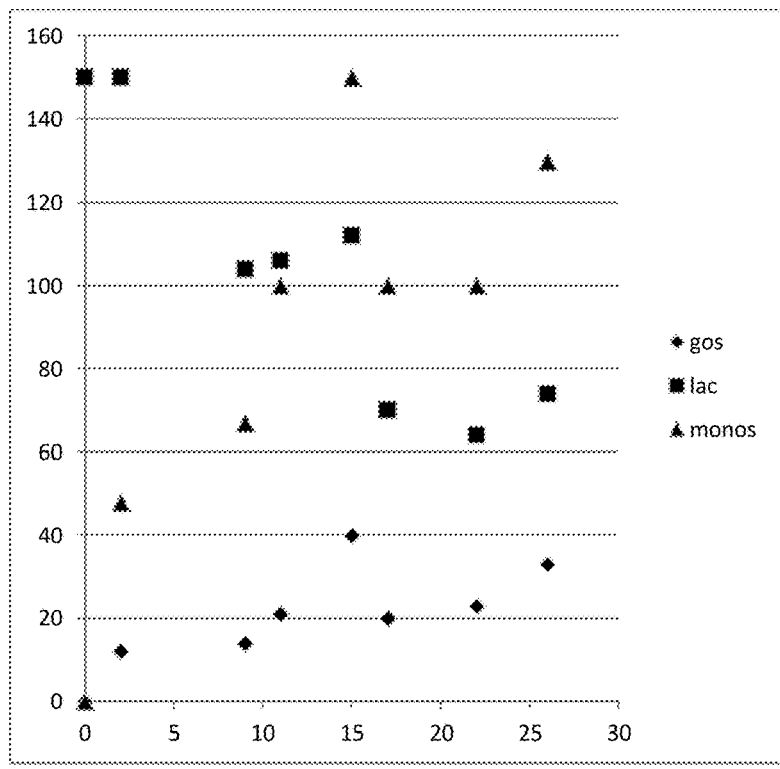
GOS%
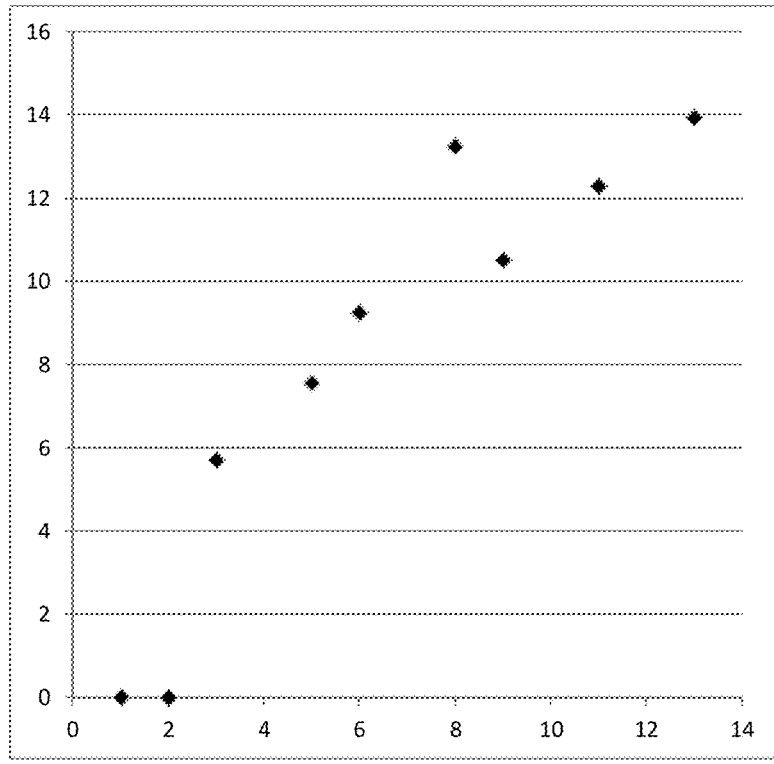

PREBIOTIC COMPOSITION AND ITS METHODS OF PRODUCTION

TECHNICAL FIELD OF THE INVENTION

The invention relates to a prebiotic composition which is specific for the growth of a desired *Lactobacillus plantarum* probiotic bacterial strain(s).

BACKGROUND TO THE INVENTION

Probiotics are bacteria which confer health benefits to a host. Typically, cultures of probiotic bacterial strains are consumed or administered to individuals in order to supplement the naturally occurring bacteria population of the gut. A number of health benefits have been associated with probiotics, including reducing the incidence of cancer, diarrhea and irritable bowel syndrome to name a few. Preliminary studies also indicate that probiotics can be useful in reducing serum levels of cholesterol and blood pressure and help modulate diabetes.

Lactobacilli are common probiotics in diary products and make up approximately 75% of probiotics currently sold. However, it has been estimated that only 2% of Lactobacilli dose survives be effective in the gut.

Prebiotics are dietary ingredients which can selectively enhance beneficial indigenous gut microbiota, such as lactobacilli or bifidobacteria, and are finding much increased application into the food sector. Prebiotics are non digestible food ingredients that are selectively metabolised by colonic bacteria which contribute to improved health. As such, their use can promote beneficial changes within the indigenous gut microbial milieu and they can therefore help survivability of probiotics. They are distinct from most dietary fibres like pectin, celluloses, xylan, which are not selectively metabolised in the gut. Criteria for classification as a prebiotic is that it must resist gastric acidity, hydrolysis by mammalian enzymes and gastrointestinal absorption, it is fermented by intestinal microflora and selectively stimulates the growth and/or activity of intestinal bacteria associated with health and well-being.

Fructo-oligosaccharides (FOS, inulin and oligofructose) and galactooligosaccharides (GOS) have been demonstrated to fulfil the criteria for prebiotic classification repeatedly in human intervention studies. Currently, no selective prebiotic for lactobacilli exists.

It is an object of the present invention to provide a prebiotic composition which allows for the specific growth of a given probiotic bacteria. It would also be desirable if the prebiotic targeted a beneficial species or strain of probiotic which is commonly used in industry, such as a *Lactobacillus plantarum* A yet further object of the present invention is to provide a screening method to identify and produce prebiotic compositions which are selective for certain probiotic bacterial strains.

SUMMARY OF THE INVENTION

In accordance with a first aspect of the present invention, there is provided A prebiotic composition comprising a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse β-galactosidase reaction in the chosen probiotic bacterial strain.

The galactooligosaccharide (GOS) may comprise homogenous or heterogeneous oligosaccharide(s).

Preferably, the GOS is produced and/or is selective for one of more of the following bacterial strains: *Lactobacillus plantarum* 2828 (ECGC 13110403); *Lactobacillus plantarum* 2830 (ECGC 13110402); and *Lactobacillus plantarum* 2691 (ECGC 13110401), or mutant strains thereof.

The prebiotic composition will preferably be present in the composition in an effective amount so as to elicit a change in the proportions of the desirable indigenous gut microbiota and in particular the preferred probiotic bacterial strain. Higher amounts may be utilised if change in the microbiota is required quickly or if the composition is being used to help seed the gut with a new bacterial strain not currently present.

The prebiotic composition may be encapsulated. Many encapsulation techniques will be apparent to the skilled addressee and the one employed will be tailored to the required stability of the prebiotic growth medium during digestive transit.

The prebiotic composition may further comprise an excipient or carrier compound to enable it to pass through the gastrointestinal environment of the body and be efficiently delivered to, and released in the lower gut. The prebiotic may be concentrated and/or freeze dried. The composition may be in a number of formats, such as a drinkable liquid and/or powder which can be mixed with a solid or liquid food stuff.

The prebiotic composition may be combined with one or more active ingredients, such as vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B 1, riboflavoin or B25 niacin or B3, pyridoxine or B6, folic acid or B9, cyanocobalimin or B12, pantothenic acid, biotin), and combinations thereof.

Minerals may include but are not limited to sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to cartotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

In accordance with a further aspect of the present invention, there is provided a prebiotic composition for use in the management of cholesterol or the treatment of high cholesterol. Alternatively or additionally, the composition may be for use in the management or treatment of a metabolic syndrome, weight management or obesity or diabetes. The composition comprising a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse β-galactosidase reaction in the chosen probiotic bacterial strain as herein above described may be used as a medicament or pharmaceutical and/or a dietary supplement.

In accordance with a further aspect of the present invention, there is provided a prebiotic composition for the treatment of high cholesterol, a metabolic syndrome, obesity or diabetes, the composition comprising a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse I-galactosidase reaction in the chosen probiotic bacterial strain.

In a yet further aspect of the present invention, there is provided a use of a prebiotic composition, in the manufacture of a medicament for the treatment of high cholesterol, a metabolic syndrome, obesity or diabetes, the composition comprising a microbially produced oligosaccharide, wherein the composition comprises a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse β-galactosidase reaction in the chosen probiotic bacterial strain.

It will be apparent to the skilled addressee that the features of the prebiotic as described in the first aspect of the invention will also be applicable and interchangeable for the composition for the management of cholesterol.

Alternative (or additionally) to a pharmaceutical or medicament, the composition may be used as a dietary supplement, a nutraceutical or a functional food. A yet further aspect of the present invention may be a prebiotic composition for a dietary supplement, a nutraceutical or a functional food, the composition comprising a galacto oligosaccharide (GOS) produced from *Lactobacillus plantarum*, wherein the GOS acts as a selective growth medium for a chosen *Lactobacillus plantarum* probiotic bacterial strain, and wherein the GOS is substantially the same as the form produced by reverse β-galactosidase reaction in the chosen probiotic bacterial strain.

It will again be apparent to the skilled addressee that the features of the prebiotic in connection with the first aspect of the invention will also be applicable and interchangeable for the composition for a dietary supplement, a nutraceutical or a functional food.

Furthermore, the composition could be incorporated into an existing food, such as yoghurt or as a powder which can be easily blended with foodstuffs or made into a liquid drink.

In another aspect of the present invention, there is provided A method of producing galacto oligosaccharide (GOS) comprising the steps of growing one or more *Lactobacillus plantarum* strains in a growth medium comprising up to about 50% lactose at a temperature of up to about 55° C. for up to 16 hours under anaerobic conditions and harvesting the GOS from the *Lactobacillus plantarum* cells.

Preferably, the one or more *Lactobacillus plantarum* strains are grown in a growth medium comprising up to about 40% lactose at a temperature of up to about 50° C. for up to about 14 hours. The one or more *Lactobacillus plantarum* strains may be grown in a growth medium comprising in the range of about 20 to about 40% lactose at a temperature in the range of about 40 to about 50° C. for about 10 to about 14 hours.

The growth medium comprises MRS media or a modified version thereof.

Preferably, the MRS media comprises: about 8 to about 12 g/L bacteriological peptone; about 7 to about 9 g/L meat extract; about 3 to about 5 g/L yeast extract; about 1 to about 3 g/L sodium phosphate monobasic; about 4 to about 6 g/L sodium acetate; about 1 to about 2 g/L triammonium citrate; about 0.1 to about 0.3 g/L $MgSO_4$; about 0.02 to about 0.1 5 g/L $MnSO_4$; about 1 to about 3 ml/L Tween 80; about 0.25 to about 0.75 g/L L cysteine HCL; about 2 to about 6 ml/L rezasurin; and about 20 to about 55% lactose.

More preferably, the MRS media comprises: up to about 10 g/L bacteriological peptone; up to about 8 g/L meat extract; up to about 4 g/L yeast extract; up to about 2 g/L sodium phosphate monobasic; about up to 5 g/L sodium acetate; up to about 2 g/L triammonium citrate; up to about 0.2 g/L $MgSO_4$; up to about 0.05 g/L $MnSO_4$; up to about 1.5 ml/L Tween 80; up to about 0.5 g/L L cysteine HCL; up to about 4 ml/L rezasurin; and up to about 50% lactose.

Most preferably, the MRS media comprises: about 10 g/L bacteriological peptone; about 8 g/L meat extract; about 4 g/L yeast extract; about 2 g/L sodium phosphate monobasic; about 5 g/L sodium acetate; about 2 g/L triammonium citrate; about 0.2 g/L $MgSO_4$; about 0.05 g/L $MnSO_4$; about 1 ml/L Tween 80; about 0.5 g/L L cysteine HCL; about 4 ml/L rezasurin; and up to about 50% lactose.

The β-galactosidase may be harvested by a number of methods, but it is preferred that is harvested from the *Lactobacillus plantarum* cells by lysis. Such a lysis may involve one or more freeze-thawing steps.

The *Lactobacillus plantarum* strains may be selected from one or more of the following: *Lactobacillus plantarum* 2828 (ECGC 13110403); *Lactobacillus plantarum* 2830 (ECGC 13110402); and *Lactobacillus plantarum* 2691 (ECGC 13110401), or mutant strains thereof.

Preferably, the yield of GOS is up to about 35%. More preferably, the yield of GOS is up to about 31%. Most preferably, the yield of GOS is up to about 30.5%.

Preferably, the conversion of lactose is up to about 70%. More preferably the conversion of lactose is up to about 68%. Most preferably, conversion of lactose is up to about 66%.

The method as hereinabove described, may be used to produce GOS for use in a compositional aspects of the present invention.

DETAILED DESCRIPTION OF THE INVENTION

Embodiments of the present invention will now be described, by way of example only, in which:

FIG. 1A is a graph of bacterial count over time using 0.1% lactose as a growth medium for *L. plantarum*;

FIG. 1B is a graph of bacterial count over time using 0.1% lactose as a growth medium for *L. casei*;

FIG. 1C is a graph of bacterial count over time using 0.1% lactose as a growth medium for *L. salivarius*;

FIG. 1D is a graph of bacterial count over time using 0.1% lactose as a growth medium for *L. fermentum*;

FIG. 1E is a graph of bacterial count over time using 0.1% lactose as a growth medium for *L. rhanmosus*;

FIG. 1F is a graph of bacterial count over time using 0.1% lactose as a growth medium for *L. delbrueckii*;

FIG. 2A is a graph of bacterial count over time using 5% lactose as a growth medium for *L. plantarum*;

FIG. 2B is a graph of bacterial count over time using 5% lactose as a growth medium for *L. casei*;

FIG. 2C is a graph of bacterial count over time using 5% lactose as a growth medium for *L. salivarius;*

FIG. 2D is a graph of bacterial count over time using 5% lactose as a growth medium for *L. delbrueckii;*

FIG. 2E is a graph of bacterial count over time using 5% lactose as a growth medium for *L. rhanmosus;*

FIG. 2F is a graph of bacterial count over time using 5% lactose as a growth medium for *L. acidophilus;*

FIG. 2G is a graph of bacterial count over time using 5% lactose as a growth medium for *L. helveticus;*

FIGS. 9 & 10 shows graphs of the quantity of Sugars (GOS, Lactose and Monosaccharides) and GOS % over time for *L. fermentum* ATCC 11976;

FIGS. 11 & 12 shows graphs of the quantity of Sugars (GOS, Lactose and Monosaccharides) and GOS % over time for *L. fermentum* NCIMB 30226;

FIG. 13 shows graphs of the quantity of Sugars (GOS, Lactose and Monosaccharides) and GOS % over time for 18U. *L. fermentum* ATCC 11976;

FIG. 14 shows graphs of the quantity of Sugars (GOS, Lactose and Monosaccharides) and GOS % over time for 18U. *L. fermentum* NCIMB 30226;

FIG. 15 shows graphs of the quantity of Sugars (GOS, Lactose and Monosaccharides) and GOS % over time for 30U. *L. fermentum* ATCC 11976;

FIG. 16 shows graphs of the quantity of Sugars (GOS, Lactose and Monosaccharides) and GOS % over time for 30U. *L. fermentum* NCIMB 30226;

Figure 31A:
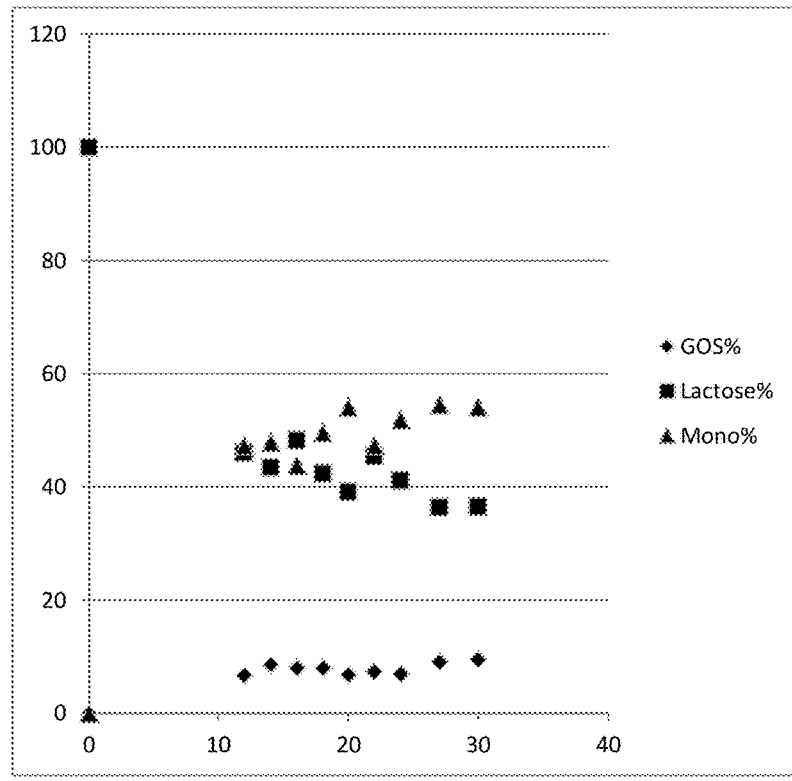
Figure 31B:
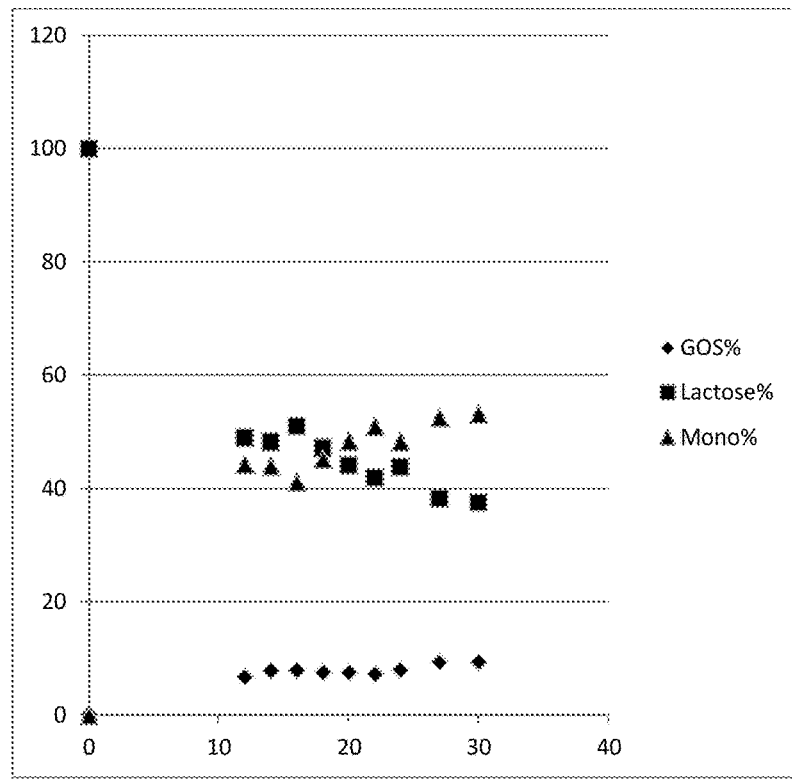
Figure 32A:
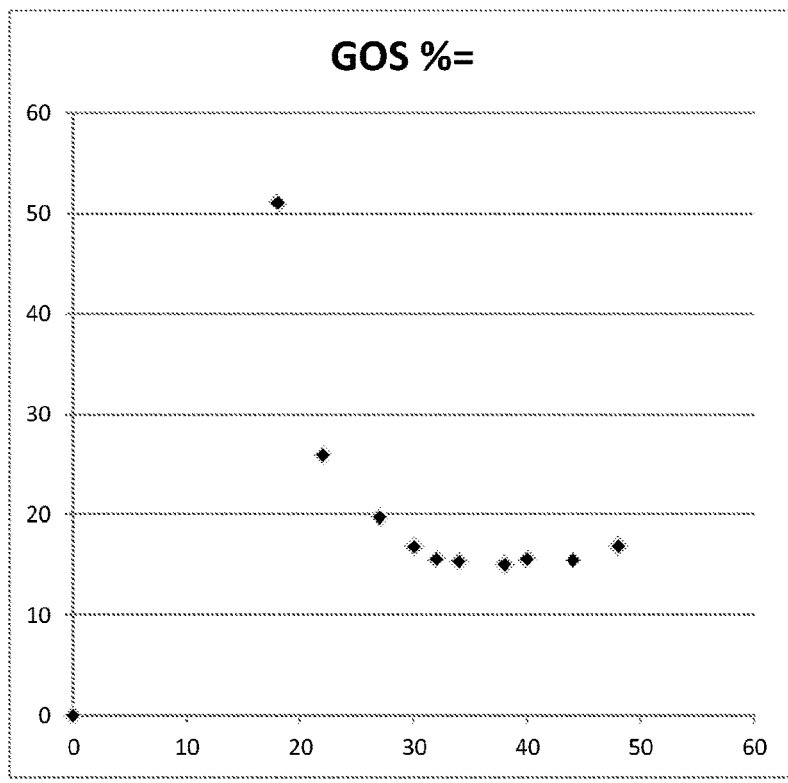
Figure 32B:
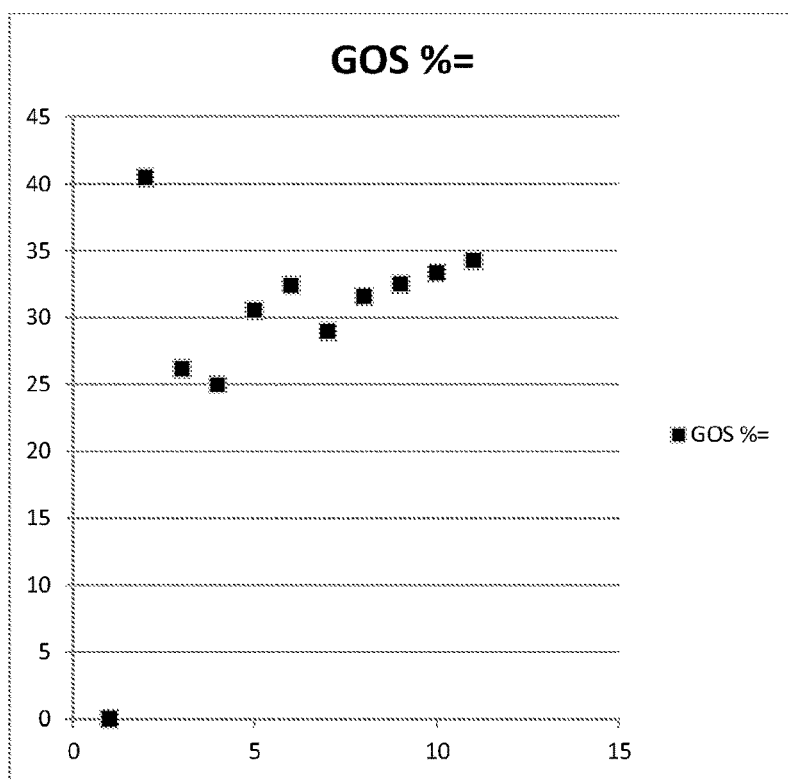

FIG. 31A and FIG. 31B show the comparatively different percentage of sugars (and GOS yield) between the *Lactobacillus fermentum* NCIMB 30226 (FIG. 31A) and *Lactobacillus fermentum* ATCC 11976 (FIG. 31B) strains when grown in 15% lactose at 40° C.; and FIG. 32A and FIG. 32B shows the comparatively different percentage of sugars (and GOS yield) between the *Lactobacillus fermentum* NCIMB 30226 (FIG. 32A) and *Lactobacillus fermentum* ATCC 11976 (FIG. 32B) strains when grown in 40% lactose at 40° C.

Mechanistically glycosidases are all transferases that use water as their preferred acceptor molecule. Under appropriate circumstance, however, such as high concentrations of substrate carbohydrate, these enzymes will transfer monosaccharide moieties from the substrate (acting as glycosyl donor) to other substrate or non-substrate carbohydrates (acting as glycosyl acceptor). Typically, the products of these reactions are complex mixtures containing all possible glycosidic linkages but in differing amounts. As the reactions are kinetically controlled, the linkage profile synthesised should map onto the rate constants for hydrolysis of those linkages by the producing enzyme. Consequently the oligosaccharides may be more readily metabolised by the producing organisms than by others in the gastrointestinal ecosystem. This approach has shown promise in laboratory testing.

It is possible, however in many enzyme synthesis reactions to include other carbohydrates which will act as acceptors in addition to the lactose. In this way, novel mixtures containing novel structures could be built up.

Probiotic species such as lactobacilli and bifidobacteria are highly saccharolytic and they frequently produce a range of glycosidase enzymes. These enzymes may have transfer activity and be able to synthesise oligosaccharides. This activity is widely reported for β-galactosidases but has not been as intensively studied for other enzymes such as α-galactosidases, α- and β-glucosidases, α-mannosidases, or β-xylosidases. It is also possible to synthesise oligosaccharides using sucrose dependant glycosyltransferases. These transfer either the fructose or glucose moiety from sucrose to sucrose acceptors and build up long polysaccharide chains. In the presence of suitable acceptors, however, they frequently synthesise hetero-oligosaccharides. This has been shown to occur with dextransucrase and alteransucrase and may also occur with laevansucrase.

The experiments sought to explore a strategy to use the products of one synthesis reaction as acceptors in a subsequent reaction. If a probiotic produces a β-galactosidase and a laevan sucrase, for instance, an enzyme extract could be used to synthesise galactooligosaccharides. This product mixture could then be used with the same extract and sucrose as glycosyl donor to bring about the synthesis of fructans—many of which would be built up on the galactooligosaccharides which would act as acceptors. In this way novel complex mixtures could be produced that should have a highly tailored fermentation by the producing organism.

The basis of the present experiments was to reversibly use β-galactosidases in microorganisms so as to produce a novel GOS. Ordinarily, β-galactosidases would digest lactose. However, by changing the reaction conditions, in terms of substrate and temperature, the enzyme acts reversibly and generates an oligosaccharide version of the lactose (GOS).

Lactobacilli are more frequently used as probiotics than are bifidobacteria, yet no prebiotic selective to lactobacilli exists. As these probiotics also harbour β-galactosidase activity, the experiments induced the production of GOS which was specific to these probiotics. The metabolism of prebiotics like GOS are species specific (as evidenced by Bi-Immuno and bifidobacteria), so a Lactobacilli GOS has the potentially enhance the growth, survivability, and health benefits of lactobacilli.

The experiments undertaken were as follows:
1. Assemble and test a range of probiotic lactobacilli for their capacity to generate GOS and measuring β-galactosidase activities;
2. Generate a prebiotic GOS using the reverse enzyme procedure;
3. Scale up of the novel molecule to allow in vitro testing;
4. Compare survival and growth of lactobacilli in the absence and presence of the prebiotic in a series of 'gut model' experiments that test the probiotics and synbiotics;
5. Assess the possibility for using GOS as encapsulation material for the lactobacilli; and
6. Test delivery properties of the encapsulation material.

The bacterial strains initially investigated during the first stage of the experiments are shown below in Table 1:

TABLE 1

| Strain | Number | Origin |
|---|---|---|
| Lactobacillus acidophilus | NCIMB 30184 | Human |
| Lactobacillus rhamnosus | NCIMB 30188 | Human |
| Lactobacillus plantarum | NCIMB 30187 | Pickled cabbage |
| Lactobacillus delbrueckii ssp. bulgaricus | NCIMB 30186 | Yogurt |
| Lactobacillus casei | NCIMB 30185 | Cheese |
| Lactobacillus salivarius ssp. salivarius | NCIMB 30225 | Human |
| Lactobacillus fermentum | NCIMB 30226 | Dairy |
| Lacobacillus helveticus | NCIMB30224 | Dairy |
| Lactobacillus fermentum | ATCC11976 | Human |
| Lactobacillus salivarius | ATCC 11741 | Human |

Bacterial growth curve determination was undertaken by sampling cultures at 0 h, 3 h, 5 h, 8 and 24 h intervals using a 100 μL of dilution series of culture in 900 μL PBS. 20 μL of each series was spread onto a jar and with a negative control and growth assessed.

Bacterial count of several of the strains was assessed by using 0.1% lactose as the growth medium. FIGS. 1A-1F show that bacterial count over time using 0.1% lactose as a growth medium for *L plantarum, L. casei, L. salivarius, L. fermentum, L. rhanmosus*, and *L. delbrueckii* all resulted in a steady growth curve from approximately 6.5 log 10 CFU/ml to just over 9.5 log 10 CFU/ml at around 13 hours and growth tailed off as it did not increase by 25 hours.

Bacterial count of several of the strains was assessed by using 5% lactose as the growth medium. FIGS. 2A-2G show the bacterial count over time using 5% lactose as a growth medium for *L. plantarum, L. casei, L. salivarius, L. delbrueckii, L. rhanmosus, L. acidophilus* and *L. helveticus*. Again, all resulted in a steady growth curve from approximately 6.5 log 10 CFU/ml to just over 9.5 log 10 CFU/ml at around 13 hours and growth was then flat as it did not increase by 25 hours.

Cholesterol was then included in the culture medium of the bacterial strains and each strain tested for quantity of cholesterol after incubation.

The cholesterol assay used relies on the following formula:

$$\% \text{ cholesterol} \times \text{dry weight (g)}^{-1} = (B - T/B \times 100)/W$$

Where B=cholesterol content in the uninoculated control mg/l$^{-1}$, T=cholesterol in culture medium mg/l$^{-1}$ and W=cells (dry weight g after 12 h of inc).

The pellet weight of the culture was measured independently of the supernatant and the spent broth (evaporated residues) also measured. The cholesterol assay was run in triplicate in several runs.

Figure 3:
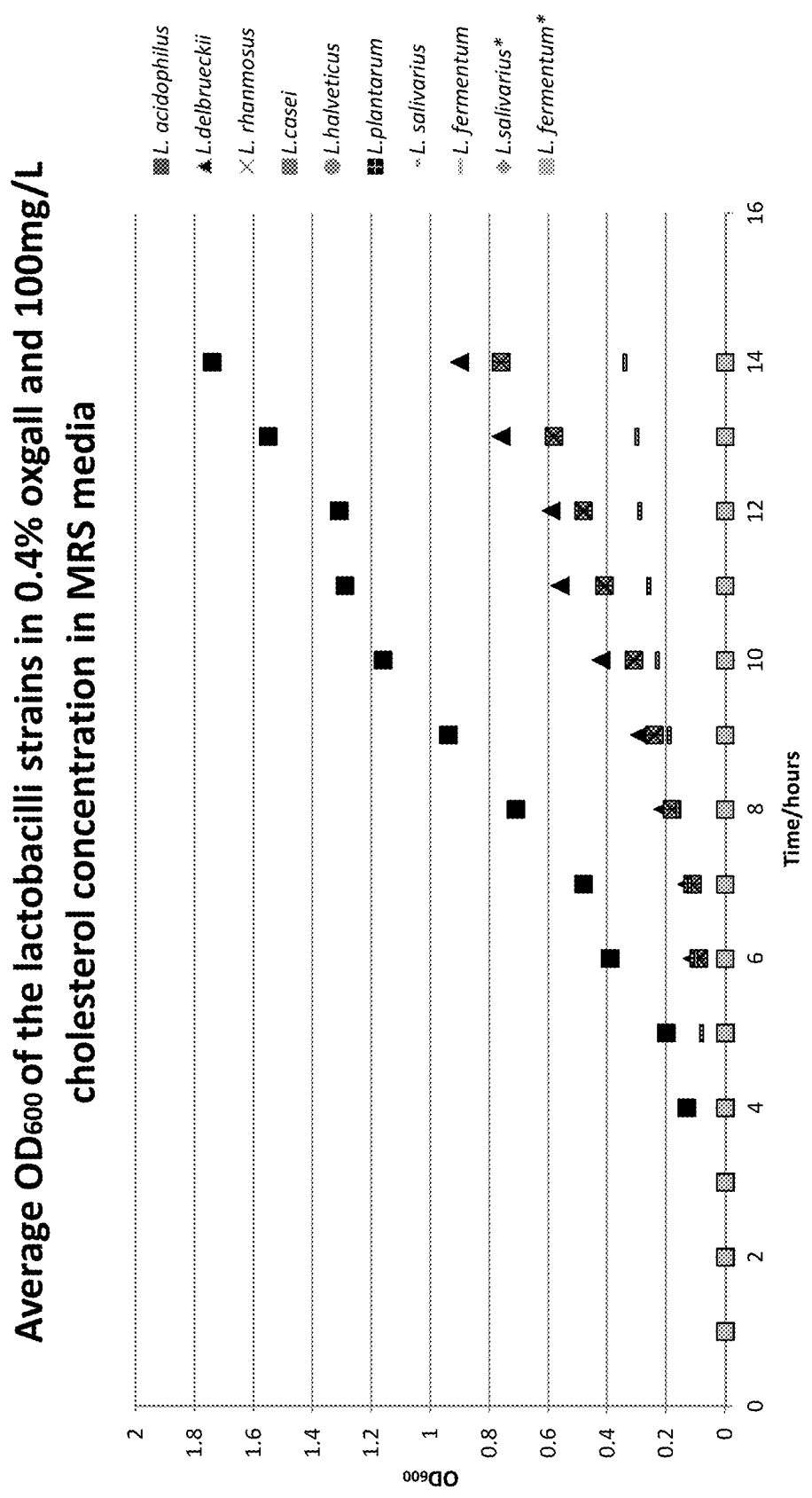
FIG. 3 is a graph showing the results of different bacterial strains over 14 hours ($OD_{600}$ measured every hour) in 0.4% oxgall and 100 mg/L cholesterol concentration in MRS media.

FIG. 3 shows the growth of different bacterial strains over 14 hours (OD$_{600}$ measured every hour) in 0.4% oxgall and 100 mg/L cholesterol concentration in MRS media and shows that some bacterial strains were much more effective at growing in this media. *L. Planatarum* showed the best growth profile, followed by *L. delbrueckii, L. casei* and *L. fermentum*. FIG. 3 shows the growth of different bacterial strains over 12 hours (OD$_{600}$ measured every hour) in 0.4% oxgall and 100 mg/L cholesterol concentration in MRS media and shows that some bacterial strains were much more effective at growing in this media. *L. planatarum* showed the best growth profile, followed by *L. delbrueckii, L. casei* and *L. fermentum*.

Figure 4:
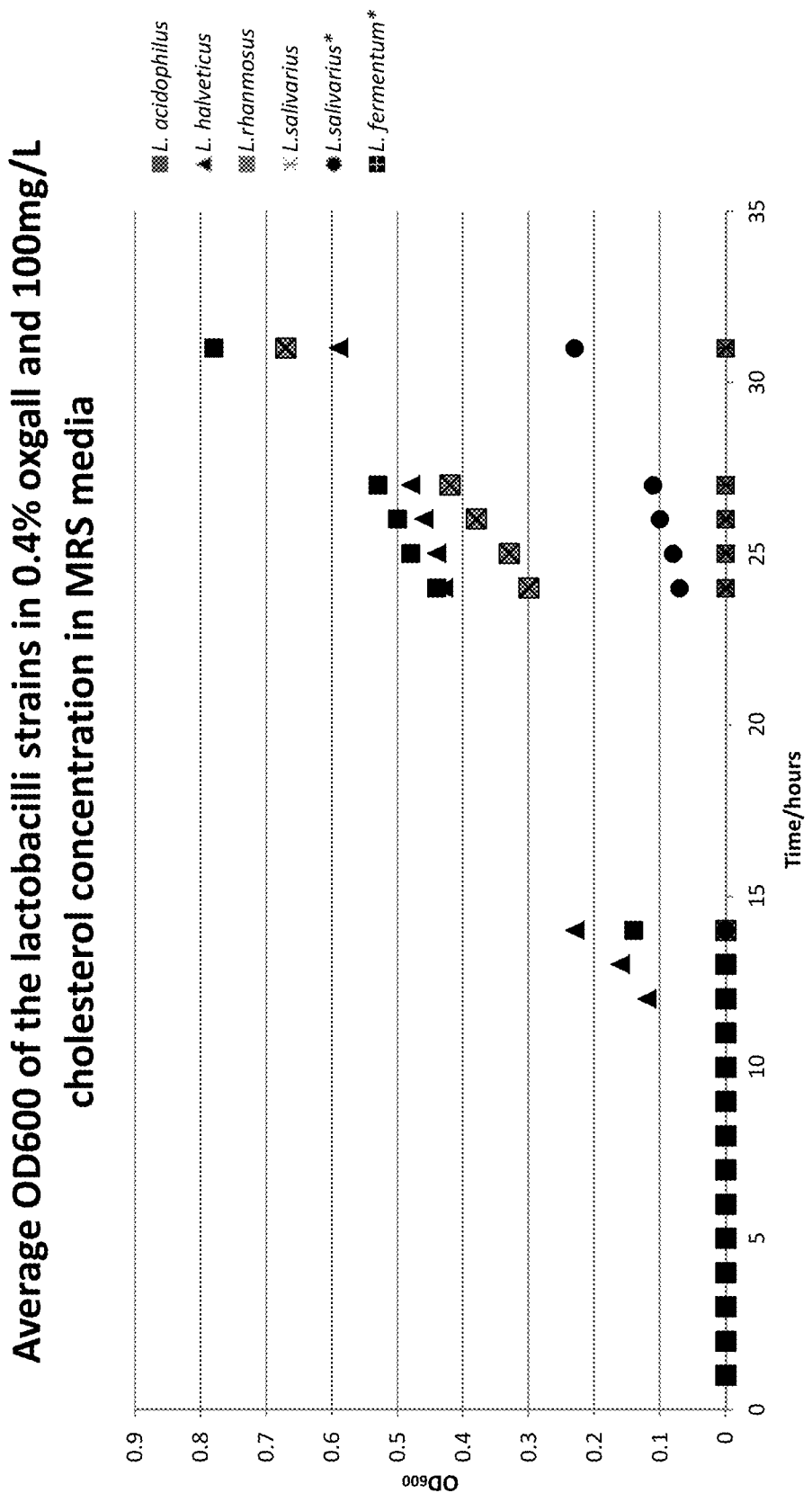
FIG. 4 is a graph showing the results of different bacterial strains over 2 days prior to testing ($OD_{600}$ measured every hour) in 0.4% oxgall and 100 mg/L cholesterol concentration in MRS media.

FIG. 4 is a graph showing the results of different bacterial strains over 2 days prior to testing (OD$_{600}$ measured every hour) in 0.4% oxgall and 100 mg/L cholesterol concentration in MRS media. *L. fermentum* showed the best growth profile, followed by *L. rhanmosus, L. halveticus, L. halveticus* and *L. salivarius*.

Direct plate assay tests were then conducted on the strains to further measure cholesterol activity. Resting cell Bile Salt Hydrolase (BSH) activity was measured to assess the release of amino acids from hydrolysis of conjugated bile acids. Bile salt deconjugation (based upon the release of free cholic acid) was measured and finally co-precipitation of cholesterol with deconjugated bile assessed. Table 2 below shows the results of the direct plate assay.

TABLE 2

| Bacteria | 1$^{st}$ run | 2$^{nd}$ run | 3$^{rd}$ run |
|---|---|---|---|
| L. casei | Y | Y | Y |
| L. delbrueckii | Y | Y | Y |
| L. acidophilus | Y | Y | Y |
| L. fermentum | X | Y | Y |
| L. salivarius | X | X | X |

TABLE 2-continued

| Bacteria | 1st run | 2nd run | 3rd run |
|---|---|---|---|
| L. halveticus | Y | X | X |
| L. rhamnosus | X | X | X |
| L. plantarum | X | Y | Y |
| L. salivarius* | X | X | X |
| L. fermentum* | X | X | Y |

It can be seen that *L. casei, L. delbrueckii* and *L. acidophilus* all had reliable BSH activity.

By comparing the results of the strains being able to grow in media containing cholesterol and those strains having BSH activity *L. casei* and *L. delbrueckii* appear to be suitable candidates for producing and identifying a specific prebiotic GOS.

The GOS prebiotic generated by a specific strain has optimised metabolism not just to produce the GOS, but also to metabolise it (as its generated from a reverse enzyme procedure). The GOS can therefore be incorporated with the probiotic into a synbiotic that would create a highly selective environment for the probiotic. As a probiotic can have a specific health benefits then a synbiotic formula which is tailored to a specific health benefit can be generated.

A screening method for identifying and formulating a synbiotic composition in accordance with an aspect of the invention follows the steps of:

(a) Identifying health need;
(b) Identifying key interjection points for probiotic action e.g BSH activity, cholesterol assimilation & heart disease;
(c) Screening probiotic library using high throughput screening methodology;
(d) Identifying strains with potential activity & health benefits;
(e) Optimising expression of activity using fermentation processes:
(f) Screening strains for beta galactosidase activity;
(g) Generating a novel GOS;
(h) Scaling up to allow in vitro testing;
(i) Comparing survival and growth of the probiotic in the absence and presence of the prebiotic using in vitro plate assays and gut model. If strain characterised then use molecular methodologies to study population changes over time. This will see if affect due to increasing number or increasing activity; and
(j) Combining pre & probiotic to explore effect of combined pre & probiotic.

Evaluation of Anaerobic Utilisation of Novel *L. reuteri* GOS

In these experiments, anaerobic cultures were tested to evaluate the in vitro utilisation of a novel *Lactobacillus reuteri* galactooligosaccharide by monitoring the populations of gut bacterial groups at 24 hours using fluorescent in situ hybridisation, and short-chain fatty acid (SCFA). Fructooligosaccharides (FOS), melibiose and raffinose were used as reference carbohydrates. Table 3 below shows the results of these experiments.

TABLE 3

| Group | Inoculum | Melibiose 24 | Melibiose 24 hr % change | Raffinose 24 | Raffinose 24 hr % change | FOS 24 | FOS 24 hr % change | GOS 24 | GOS 24 hr % change | GOS + L. acidophilus 24 | GOS + L. acidophilus 24 hr % change | GOS + L. reuterri 24 | GOS + L. reuterri 24 hr % change |
|---|---|---|---|---|---|---|---|---|---|---|---|---|---|
| Total count | 8.84 | 9.14 | 103% | 9.19 | 104% | 9.2 | 104% | 9.12 | 103% | 9.55 | 108% | 9.34 | 106% |
| Bifidobacteria | 6.85 | 7.33 | 107% | 7.69 | 112% | 7.47 | 109% | 7.69 | 112% | 7.83 | 114% | 8.19 | 120% |
| Bacteroides | 7.98 | 7.9 | *99%* | 8.08 | 101% | 8.08 | 101% | 7.95 | 100% | 8.01 | 100% | 7.89 | *99%* |
| Lactobacilli | 7.15 | 7.43 | 104% | 7.45 | 104% | 7.32 | 102% | 7.69 | 108% | 7.67 | 107% | 7.73 | 108% |
| Clostridia | 7.55 | 7.65 | 101% | 7.81 | 103% | 8 | 106% | 7.23 | *96%* | 7.48 | *99%* | 7.2 | *95%* |
| E. coli | 8.14 | 7.66 | *94%* | 8.03 | *99%* | 7.85 | *96%* | 8.04 | *99%* | 8.24 | 101% | 7.96 | *98%* |
| Eubacteria | 8.06 | 7.84 | *97%* | 8.69 | 108% | 8.27 | 103% | 7.75 | *96%* | 8.16 | 101% | 8.28 | 103% |

(Key: BOLD = Significant Increase; Italics = Significant Decrease)

The results show the *Lactobacillus reuterri* GOS showed a significant increase in bifidobacteria and lactobacilli population numbers exhibiting a prebiotic affect. In addition, the GOS increased the growth rate of lactobacilli by 108%, more than any other sugar suggesting a genus specificity. Addition of a strain of *Lactobacillus reuterri* increased the prebiotic affect, increasing the *bifidobacterium* population by 120%.

This suggests that the addition of a GOS producing organism to the GOS produced by that organism had a greater effect on the gut microflora population than the GOS alone.

Lactobacilli β-Galactosidase Screening Assay

Figure 5A:
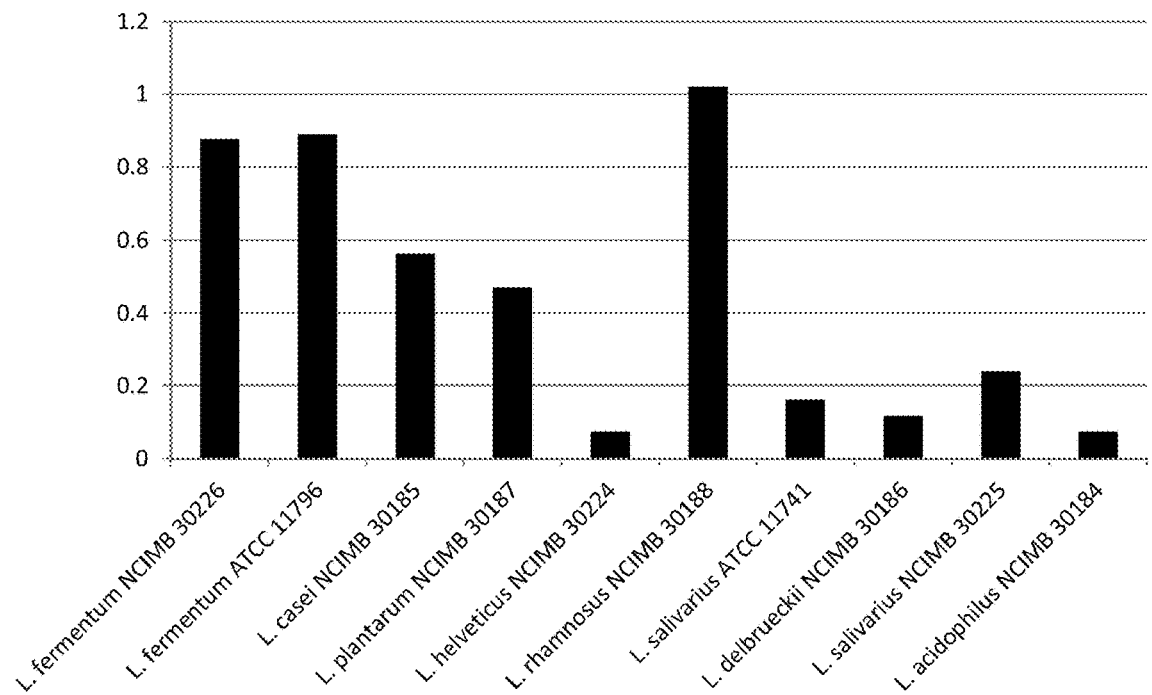
FIG. 5A-5C are graphs show the results of a range of lactobacilli species which were screened for β-galactosidase activity measured at $OD_{420}$ in A MRS broth, B 1% lactose basal media and C 5% lactose basal media.
Figure 5B:
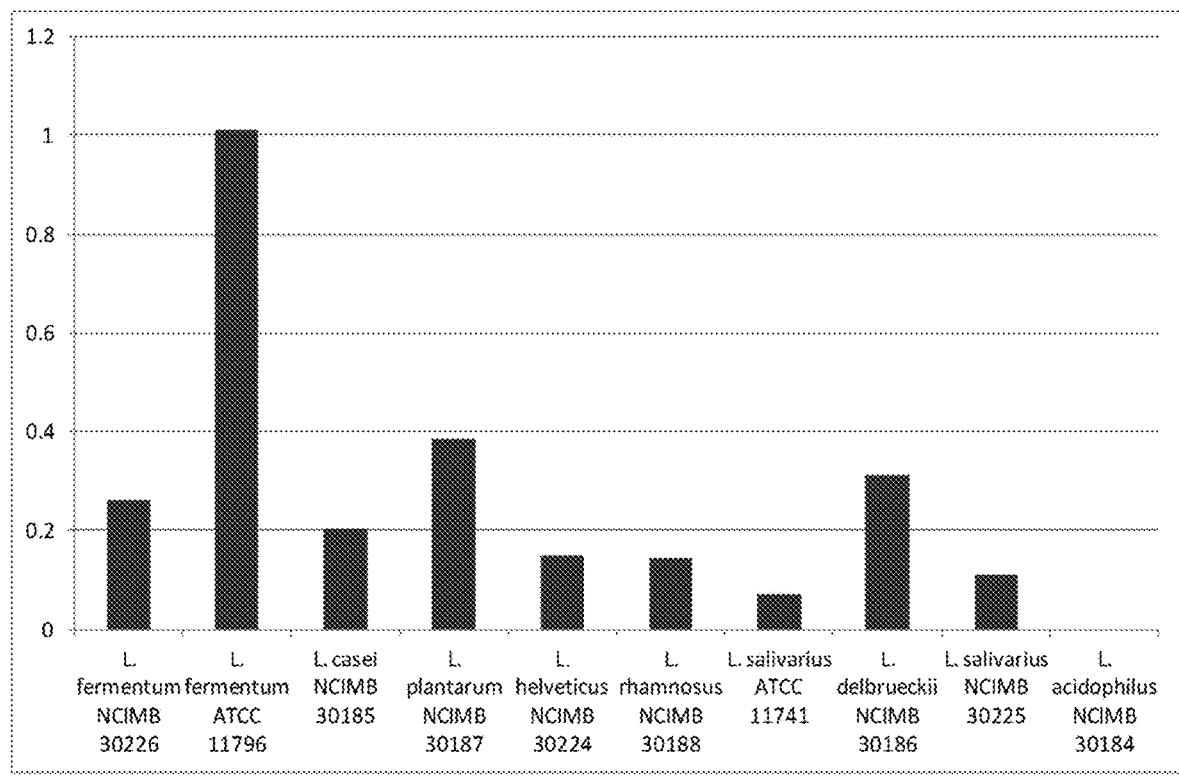
Figure 5C:
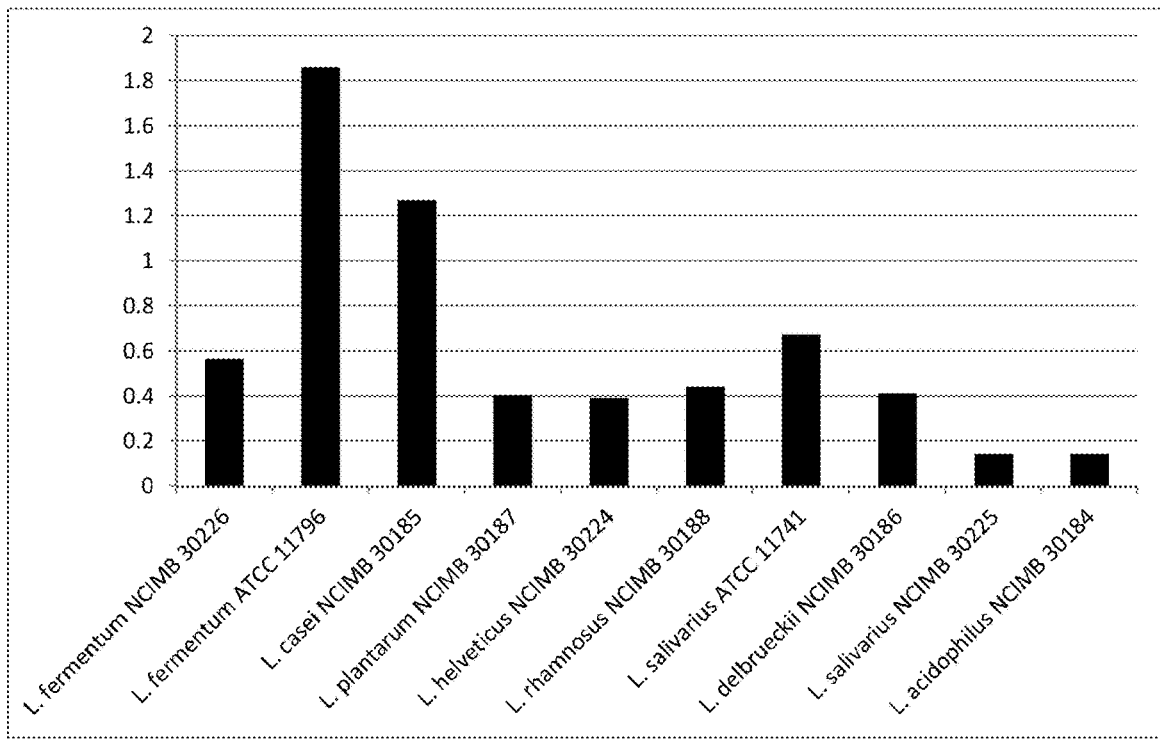
Figure 6A:
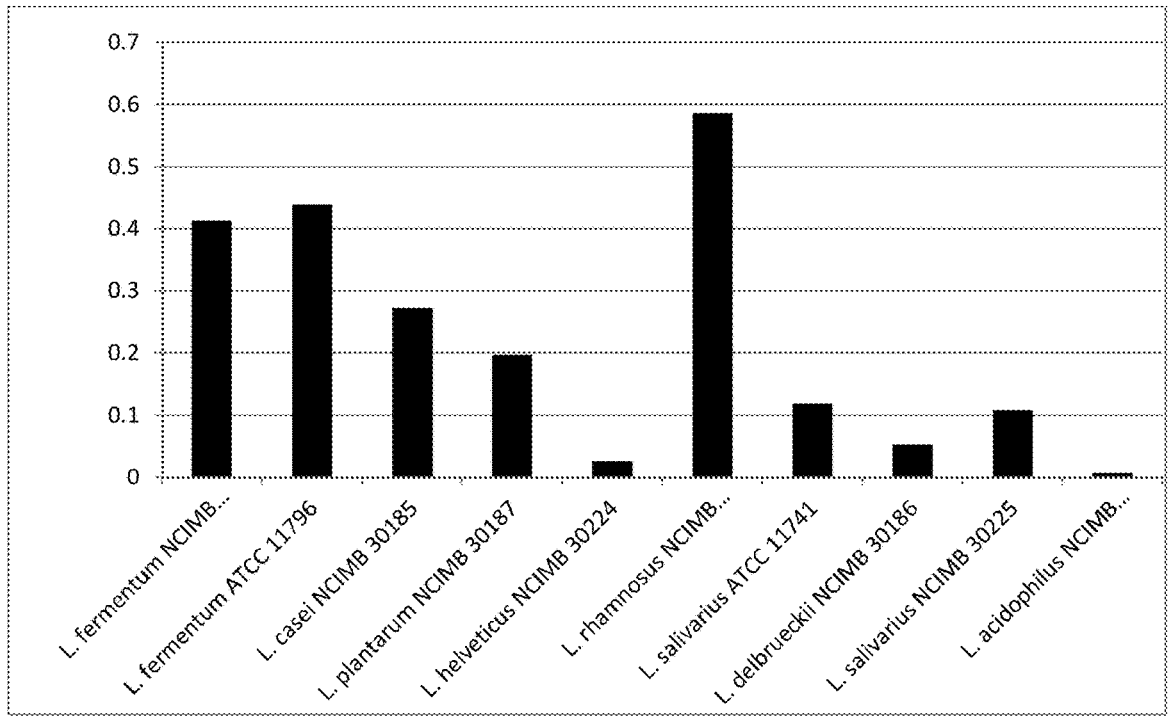
FIG. 6A-6C are graphs show the results of a range of lactobacilli species which were screened for β-galactosidase activity measured at uM of o-NP in A MRS broth, B 1% lactose basal media and C 5% lactose basal media.
Figure 6B:
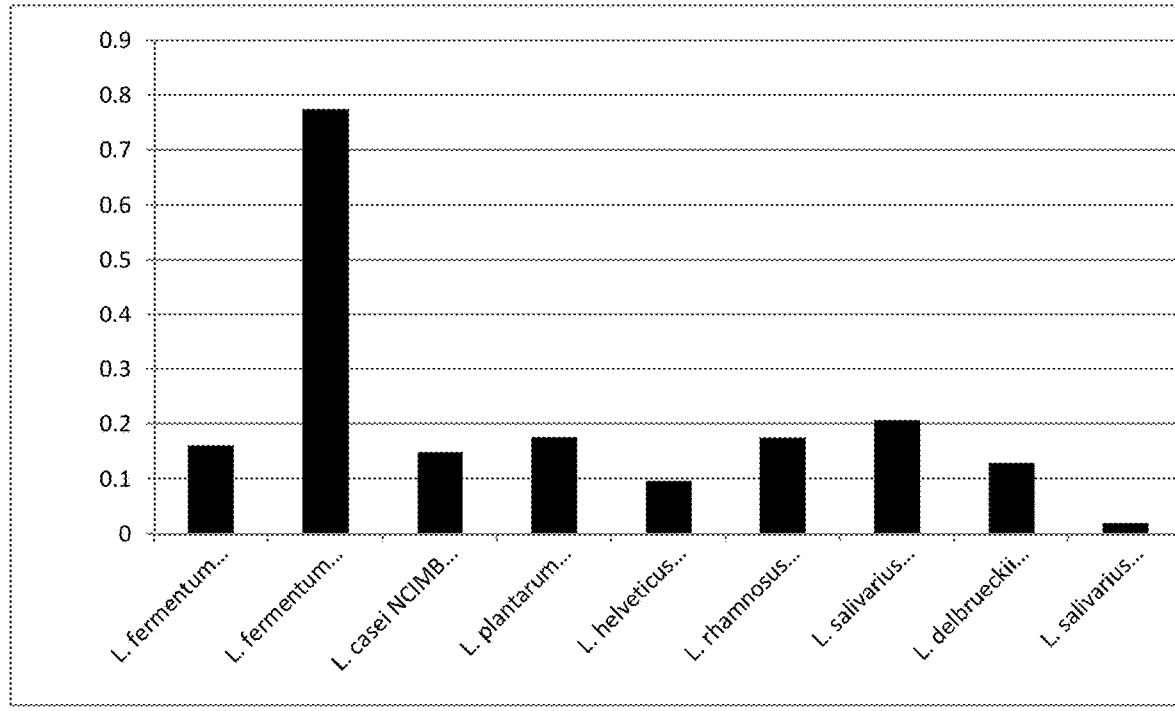
Figure 6C:
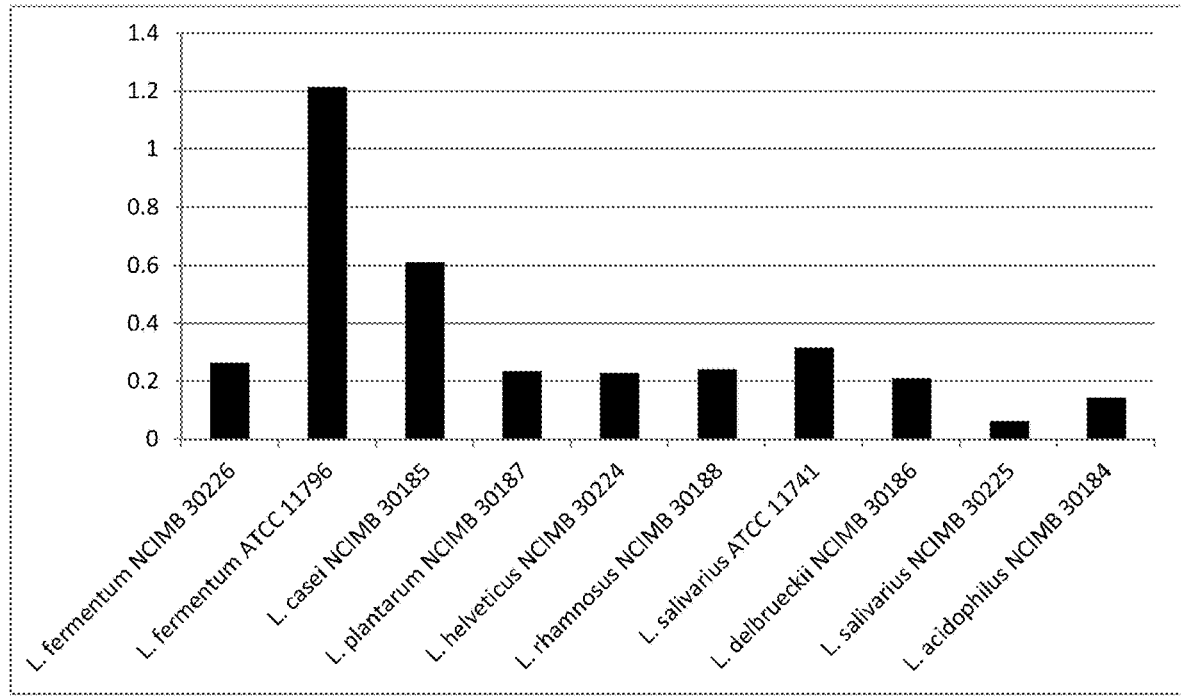

In these experiments, 10 lactobacilli species were screened for β-galactosidase activity in triplicate using standard enzyme assay with o-NPG as substrate. The experiments were carried out in 3 different media; MRS, 1% and 5% lactose in basal media, as lactose is the primary substrate for β-galactosidase it was expected to exhibit highest activity. Activity was measured at time points between time 0-24 hrs. highest activity was shown after 24 hrs. As shown in FIGS. 5-6, in general, 5% lactose exhibits highest enzyme activity and tends to be higher than in MRS broth (contains only glucose as carbon source). High enzyme activity is essential for generating GOS, the 3 organisms which show overall high activity include both *L. fermentum* strains and *L. casei*.

GOS Produced from *L. fermentum* ATCC 11976 and *L. fermentum* NCIMB 30226 in a Long Time Period In these experiments, *L. fermentum* ATCC 11976 and *L. fermentum* NCIMB 30226 were assessed for their production (and consumption) of GOS, lactose and monosaccharides over 168 hours.

Figure 7:
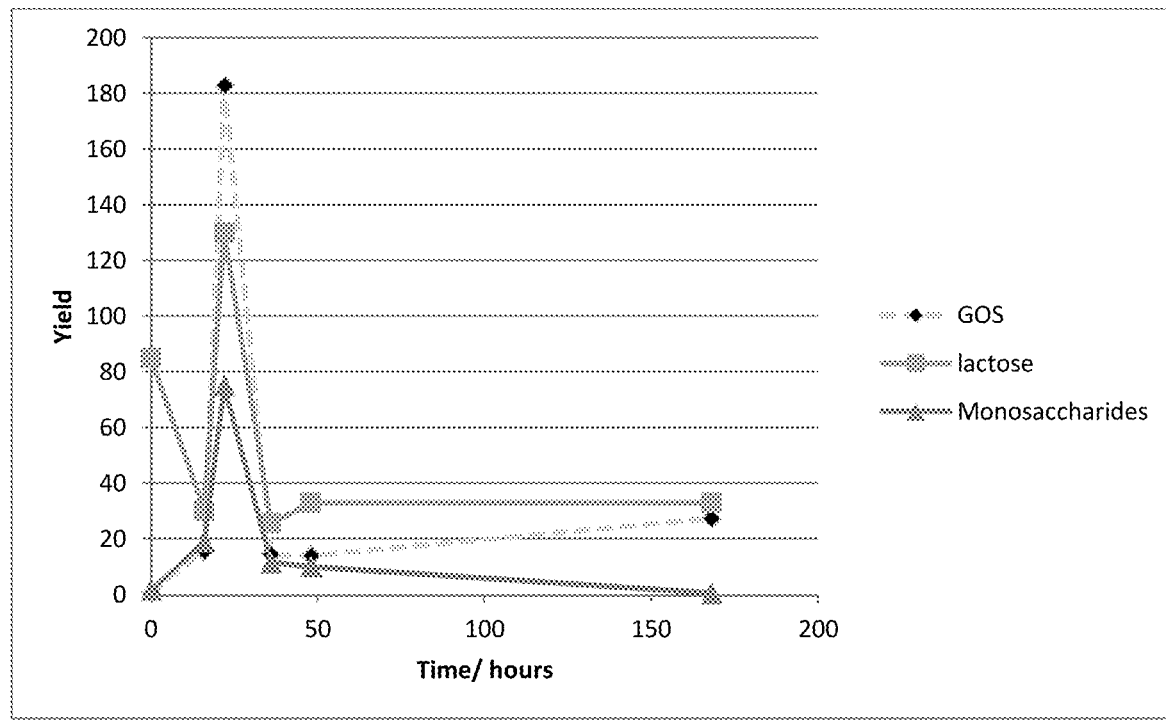
FIG. 7 is a graph showing the yield of GOS, lactose and monosaccharides by *L. fermentum* ATCC 11976 over 168 hours.

The yield of GOS, lactose and monosaccharides for *L. fermentum* ATCC 11976 is shown in the below in Table 4 and in FIG. 7:

TABLE 4

| Time point | GOS | lactose | Monosaccharides | Total | GOS %= |
|---|---|---|---|---|---|
| 0 | 0.601 | 85 | 1.464 | 87.065 | 0.690289 |
| 16 | 15.65 | 30.077 | 18.92 | 64.647 | 24.20839 |
| 22 | 183 | 130 | 75 | 388 | 47.16495 |
| 36 | 14.4 | 25.6 | 11.45 | 51.45 | 27.98834 |
| 48 | 14 | 33 | 10 | 57 | 24.5614 |
| 168 | 27.4 | 32.971 | 0.5 | 60.871 | 45.01322 |

Figure 8:
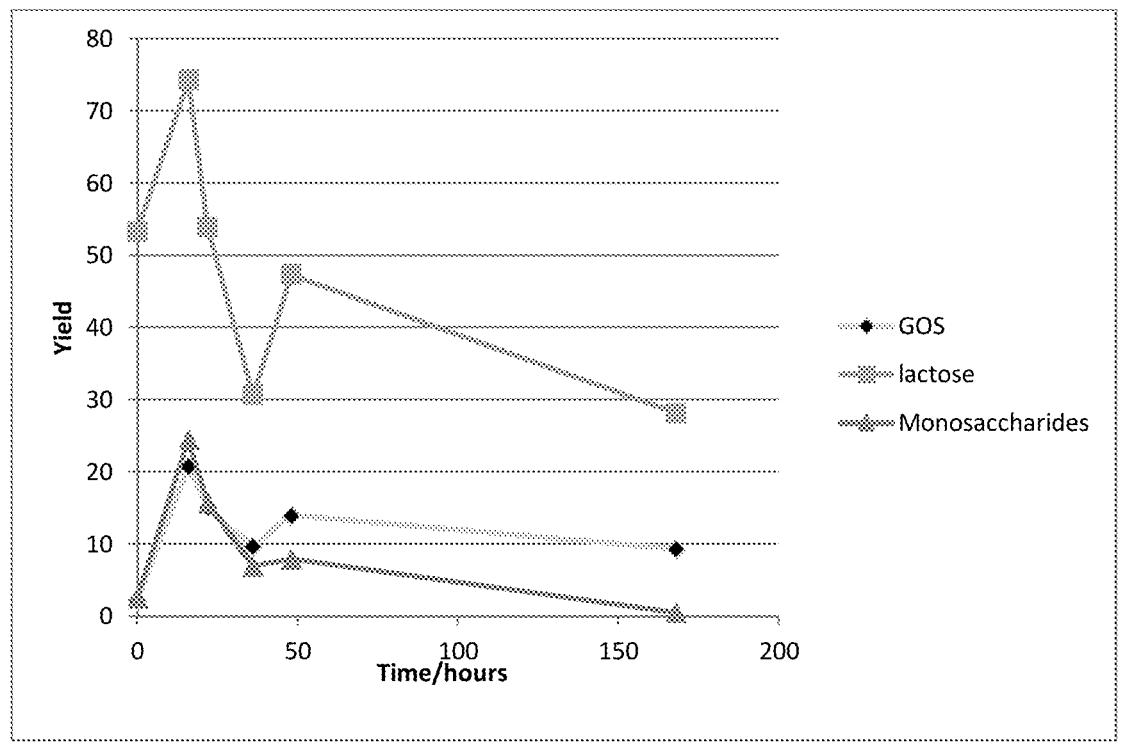
FIG. 8 is a graph showing the yield of GOS, lactose and monosaccharides by *L. fermentum* NCIMB 30226 over 168 hours.

The yield of GOS, lactose and monosaccharides for *L. fermentum* NCIMB 30226 is shown in the below in Table 5 and in FIG. 8:

TABLE 6-continued

| No. | Ret. Time min | Height v | Width min | Type | Asym. (EP) | Plates (EP) | |
|---|---|---|---|---|---|---|---|
| 4 | 8.436 | 1.465 | n.a. | Ru | n.a. | n.a. | |
| 5 | 9.072 | 1.234 | n.a. | Ru | n.a. | n.a. | |
| 6 | 10.716 | 13.758 | 1.419 | BMb | 0.87 | 851 | |
| 7 | 14.403 | 0.605 | n.a. | Ru | n.a. | n.a. | |
| 8 | 18.457 | 16.603 | n.a. | bM | n.a. | n.a. | |
| 9 | 18.694 | 17.001 | n.a. | M | n.a. | n.a. | |
| 10 | 22.318 | 0.373 | n.a. | Ru | n.a. | n.a. | |
| 11 | 24.168 | 29.345 | 29.609 | M | n.a. | n.a. | |
| 12 | 28.157 | 150.287 | 1.544 | MB | n.a. | 5436 | Lactose |
| n.a. | n.a. | n.a. | n.a. | n.a. | n.a. | n.a. | |
| Average: | | 19.424 | 10.857 | | 0.87 | 3144 | |

Table 7 below shows the sugars present at T24:

TABLE 7

| Ret.Time min | Height v | Width min | Type | Resol. (EP) | Asym. (EP) | Plates (EP) | |
|---|---|---|---|---|---|---|---|
| 2.506 | 0.010 | n.a. | BMB | n.a. | 1.52 | 128 | |
| 6.903 | 0.097 | n.a. | BM | n.a. | n.a. | n.a. | |
| 10.624 | 10.367 | 1.121 | M | 1.75 | n.a. | 1425 | |
| 15.062 | 3.082 | 3.812 | MB | 2.17 | n.a. | 232 | |
| 20.868 | 1.220 | 1.268 | BMB | 2.66 | 0.65 | 3522 | |
| 24.177 | 10.614 | 1.097 | BMb | 3.50 | 1.57 | 7869 | GOS |
| 28.167 | 73.205 | 1.207 | bM | n.a. | 1.45 | 8860 | Lactose |
| 29.600 | 5.009 | 2.231 | M | n.a. | n.a. | n.a. | |
| 32.806 | 10.232 | 1.873 | M | 1.05 | n.a. | 5038 | Glucose |
| 34.822 | 8.609 | 2.038 | M | n.a. | n.a. | 4812 | Galactose |
| 41.161 | 0.867 | n.a. | M | n.a. | n.a. | n.a. | |
| 43.560 | 0.590 | n.a. | M | n.a. | n.a. | n.a. | |
| 46.616 | 0.386 | n.a. | M | n.a. | n.a. | n.a. | |
| 49.693 | 0.107 | n.a. | MB | n.a. | n.a. | n.a. | |
| 51.010 | 0.006 | n.a. | bMB | n.a. | n.a. | n.a. | |
| 54.025 | 0.006 | n.a. | BMB | 1.18 | 1.41 | 774387 | |
| 54.751 | 0.008 | n.a. | BMB | n.a. | 1.27 | 48500 | |
| n.a. | n.a. | n.a. | n.a. | n.a. | n.a. | n.a. | |
| | 7.319 | 1.831 | | 2.05 | 1.31 | 85477 | |

TABLE 5

| Time point | GOS | lactose | Monosaccharides | Total | GOS %= |
|---|---|---|---|---|---|
| 0 | 2.206 | 53.309 | 2.538 | 58.053 | 3.799976 |
| 16 | 20.789 | 74.275 | 24.481 | 119.545 | 17.3901 |
| 22 | 15.066 | 53.918 | 15.713 | 84.697 | 17.78812 |
| 36 | 9.699 | 30.672 | 6.977 | 47.348 | 20.4845 |
| 48 | 13.971 | 47.341 | 7.944 | 69.256 | 20.17298 |
| 168 | 9.3 | 28.125 | 0.521 | 37.946 | 24.50851 |

GOS Produced from *L fermentum* ATCC 11976 in a 20% Lactose Medium Over 24 Hours In this experiment, GOS synthesis from *L. fermentum* ATCC 11976 B-galactosidase was investigated. After lysis, the crude extract was incubated in 20% lactose over 24 hr and samples taken at time 0 and 24.

Table 6 below shows the sugars present at T0:

TABLE 6

| No. | Ret. Time min | Height v | Width min | Type | Asym. (EP) | Plates (EP) |
|---|---|---|---|---|---|---|
| 1 | 0.226 | 0.397 | n.a. | BM | n.a. | n.a. |
| 2 | 0.689 | 0.283 | n.a. | MB | n.a. | n.a. |
| 3 | 6.912 | 1.743 | n.a. | Ru | n.a. | n.a. |

GOS Produced from *L. fermentum* ATCC 11976 and *L. fermentum* NCIMB 30226 in a Short Time Period In this experiment, GOS was produced from *L. fermentum* ATCC 11976 and *L. fermentum* NCIMB 30226 and the enzyme activity of the sugars vs the % GOS assessed over 50 hours as this was when most activity took place during the previous experiments.

Protocol

GOS was produced using the following protocol:
1. Set up 50 ml overnight cultures in modified MRS broth supplemented with 2% lactose for *L. fermentum* ATCC 11976 and *L. fermentum* NCIMB 30226:
2. Suspend 50 ml of overnight culture in 1 L of mMRS broth with 2% lactose;
3. Incubate in anaerobic cabinet at 37° C.;
4. *L. fermentum* ATCC 11976 for 14 hours;
5. *L. fermentum* NCIMB 30226 for 8 hours;
6. Measure $OD_{600}$;
7. Centrifuge cultures, 10 000 g×10 mins;
8. Make up 40% lactose in sodium phosphate buffer. 400 g/L;
9. Pour off supernatant;
10. Resuspend pellets in sodium phosphate buffer (50 mM, pH 6.8);
11. Pool pellets in 50 ml falcons;
12. Freeze thaw in Liquid Nitrogen ×3;
13. French Press, 30,000 PSI, 1 pass, 5 drops/min;

14. Spin down lysate—15,000 g×45 min;
15. Pour supernatant into fresh falcon;
16. Carry out β gal activity assay to work enzyme concentrations;
17. Incubate the free cell extract with 40% lactose/sodium phosphate buffer;
18. Sample 200 μl every 2 hours over 50 hours:
19. Freeze samples;
20. Filter sterilise all samples through 0.2 μm filter;
21. Analyse on HPLC.

Results—GOS Production

As shown in FIGS. 9 to 12, there was a 30-45% lactose conversion and 10% GOS yield.

Enzyme Activity

A further experiment was conducted in order to ascertain the enzyme activity (and therefore efficiency) of the GOS produced from *L. fermentum* ATCC 11976 and *L. fermentum* NCIMB 30226.

Cultures were grown for 8 hrs F, 14 hr for F* in 1 L and harvested at 12,000 g×10 min. The cells were lysed and cell extract spun down 15,000 g×45 min. This was then incubated at 40° C. in 40% lactose sodium phosphate buffer+ $MgCl_2$ with same U of enzyme/reaction and activity analysed on an HPLC at 2 hour time points for 36 hours.

The enzyme unit calculations were as follows in Table 8 below:

TABLE 8

| Organism | OD pre harvest | $OD_{420}$ (enzyme) after french press | $OD_{420}$ (enzyme) after final spin | Enzyme U/15 ml |
|---|---|---|---|---|
| F*1 | 0.83 | 2.4605 | 2.3315 | 18.23977 |
| F*2 | 0.86 | 1.83 | 3.1955 | 30.17002 |
| F1 | 0.94 | 1.833 | 3.812 | 30.0665 |
| F2 | 1.13 | 1.5739 | 6.0115 | 47.63684 |

(Where F*1, F2 18 U/reaction, F*2, F1 30 U/reaction)

Results

As shown in FIGS. 13 to 16, there was a 40-50% lactose conversion and 15-20% GOS yield.

Lactobacilli Specificity with GOS Purity

In this experiment, GOS produced from *L. fermentum* ATCC 11976 used as part of the growth media for a range of bacteria to see if this species specific GOS provided any growth specificity.

GOS Synthesis

*L. fermentum* ATCC 11976 was grown in modified MRS supplemented with 2% lactose in 1 L cultures for 14 hours. The culture was spun down and re-suspend in a sodium phosphate buffer. The cells were lysed using liquid Nitrogen and a French Press and the lysate spun to obtain free cell extract. The free cell extract was incubated with 40% Lactose and a sample taken every 2 hours over 50 hours. Samples were loaded on HPLC after every time point for analysis.

Growth Curves 20% GOS Mixture

1% of the impure GOS produced earlier was added to 9 ml mMRS hungates. The growth of a range of organisms were on this mixture were analysed: *Clostridium difficile, Bifidobacterium bifidum, Bifidobacterium longum, Lactobacillus fermentum* ATCC 11976, *Lactobacillus fermentum, Lactobacillus rhamnosus, Lactobacillus casei* & *Lactobacillus delbrueccki*. Experiments were conducted in 3 repeats in triplicate with enumeration at 0, 3, 6, 8, 16 and 24 hours.

Figure 17:
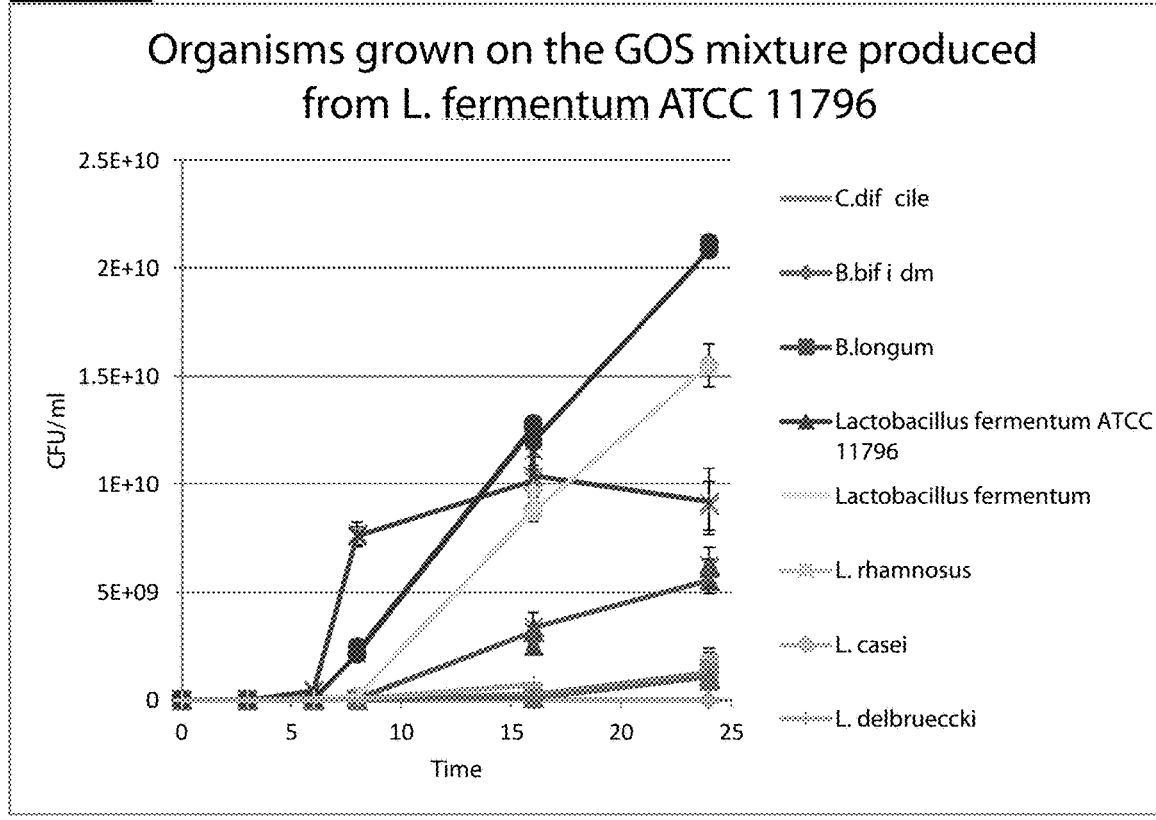
FIG. 17 is a graph illustrating the relative growth profiles of a range of bacteria grown on a GOS mixture produced from *L. fermentum* ATCC 11976.
Figure 18:
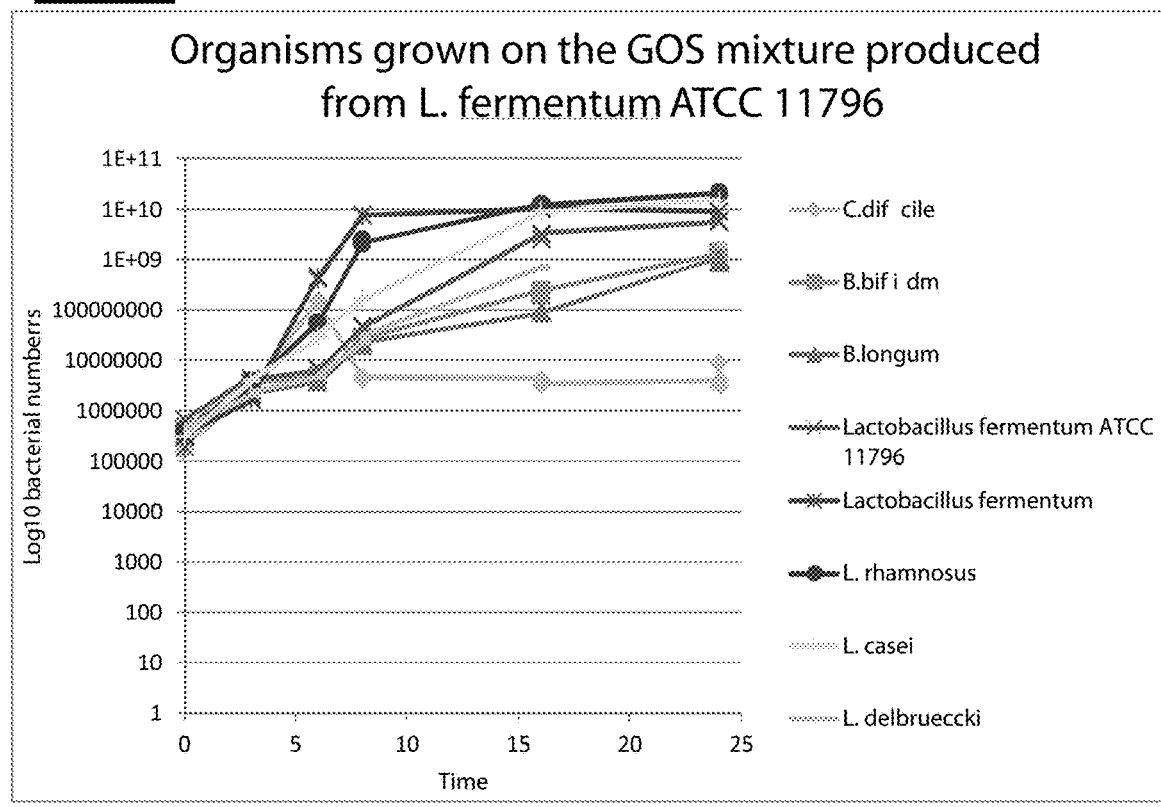
FIG. 18 is a second graph illustrating the relative growth profiles of a smaller range of bacteria grown on a GOS mixture produced from *L. fermentum* ATCC 11976.

As shown in FIGS. 17 and 18, little growth was found in *C. difficile*, whereas the best growth was found in *L. rhamnosus*. The 20% GOS mixture as generally more selective towards lactobacilli.

GOS Synthesis Optimisation

Optimisations studies were then conducted in respect *Lactobacillus fermentum* ATCC 11976, *Lactobacillus fermentum* NCIMB 30226 and *Lactobacillus plantarum* 2830 (ECGC 13110402).

A modified MRS media having the following components was used as the growth medium: Bacteriological peptone 10 g/L; Meat extract 8 g/L; Yeast extract 4 g/L; Sodium phosphate monobasic 2 g/L; Sodium acetate 5 g/L; Triammonium citrate 2 g/L; $MgSO_4$ 0.2 g/L; $MnSO_4$ 0.05 g/L; Tween 80 1 ml/L; L cysteine HCL 0.5 g/L; rezasurin—4 ml/L; and supplemented with 2% lactose.

Initial Steps

Initial steps were taken to establish the optimum time for β-Galactosidase (B gal) expression during the growth phase. The method was as follows. Firstly, the cells were grown in the modified MRS (mMRS) (as detailed above) in 10 ml, anaerobically in hungate tubes at 37° C. Samples were then taken at 0, 2, 4, 6, 8, 12, 16 and 24 hour intervals and B gal activity assays conducted at each timepoint so as to establish the optimum times for enzyme expression.

B Gal Activity Assay

Figure 19:
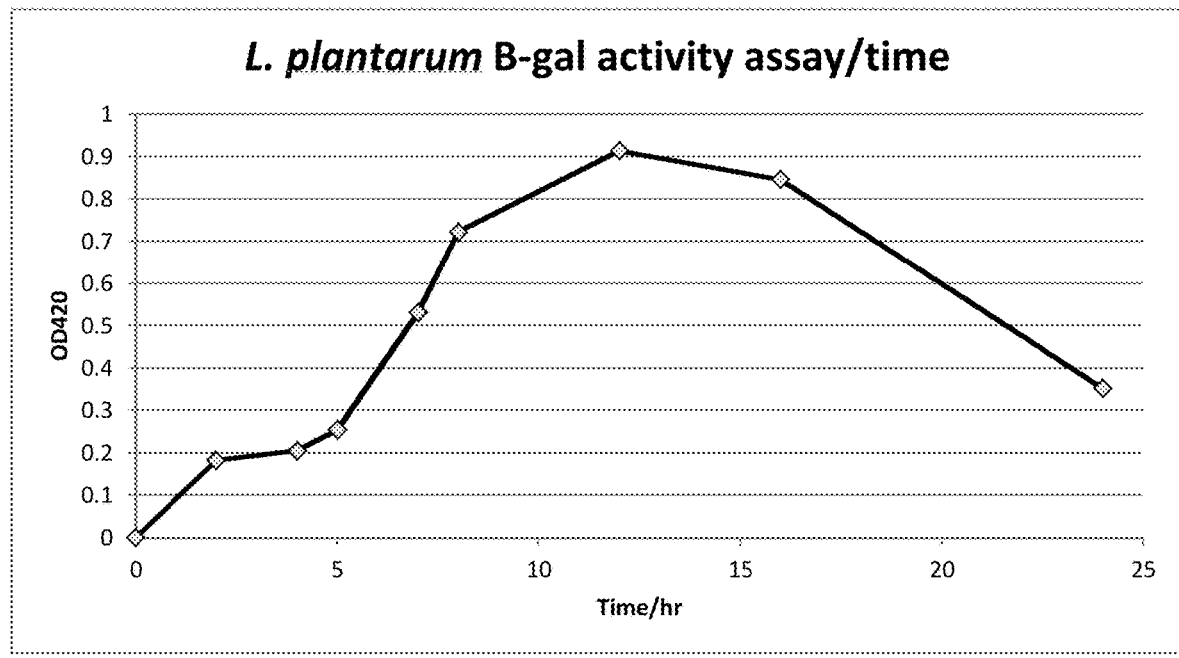
FIG. 19 shows a graph of the $OD_{420}$ measurement graph of *Lactobacillus plantarum* 2830 (ECGC 13110402) to assess B-gal activity.
Figure 20:
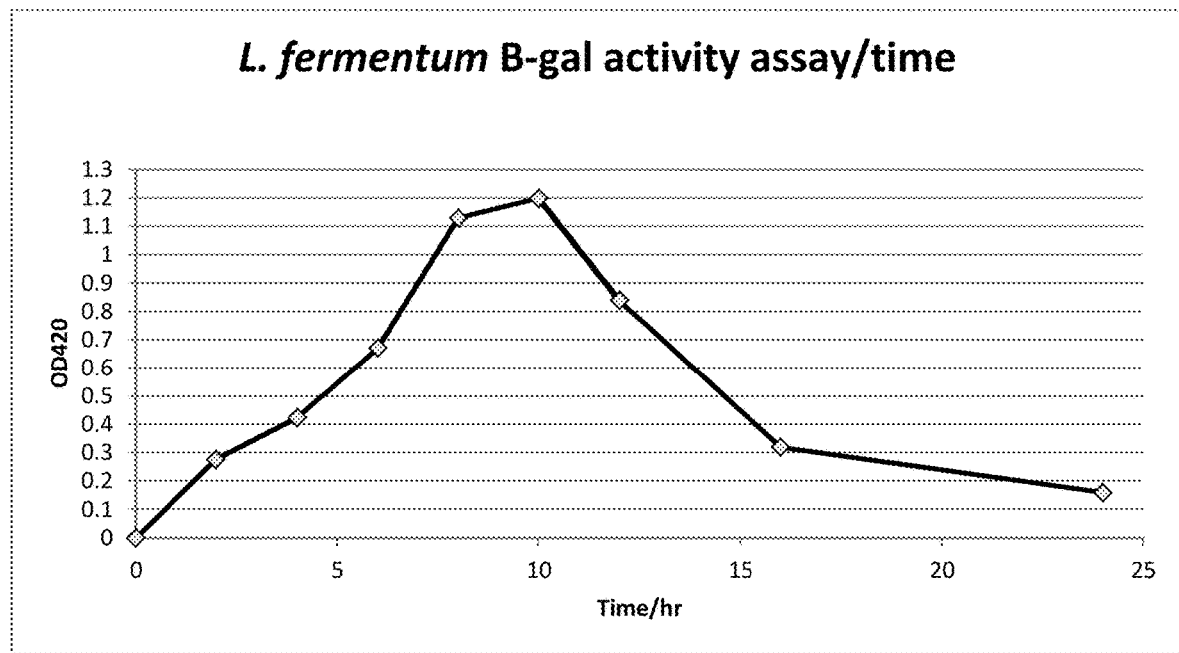
FIG. 20 shows the $OD_{420}$ measurement graph of *Lactobacillus fermentum* NCIMB 30226 to assess B-gal activity.
Figure 21:
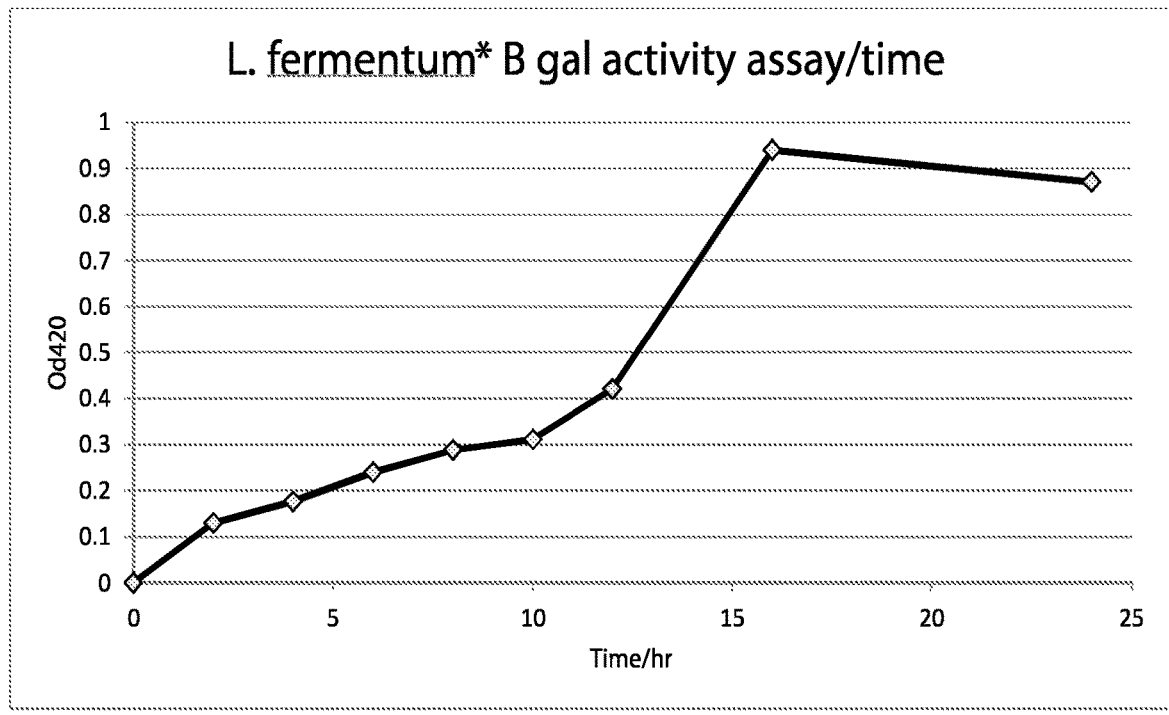
FIG. 21 shows the $OD_{420}$ measurement graph of *Lactobacillus fermentum* ATCC 11976 to assess B-gal activity.

The following reagents were used: Sodium phosphate buffer (50 mM, pH 6.8); Magnesium chloride (50 mM); Sodium carbonate (1M); O—NPG (0.2M); and For the calibration curve-o-NP (10 mM). 250 μl o-NPG, 20 μl $MgCl_2$, 200 μl buffer and 40 μl enzyme sample were incubated at 37° C. for 8 min at 120 rpm. 500 μl of sodium carbonate was then added and the sample measured at $OD_{420}$ to assess the amount of o-nitrophenol and therefore establish the B gal activity by comparing the result against calibration curve. FIG. 19 shows the $OD_{420}$ measurement of *Lactobacillus plantarum* 2830 (ECGC 13110402), FIG. 20 shows the $OD_{420}$ measurement of *Lactobacillus fermentum* NCIMB 30226, whereas FIG. 21 shows the $OD_{420}$ measurement of *Lactobacillus fermentum* ATCC 11976. B gal activity peaked at around 12 hours for *Lactobacillus plantarum* 2830 (ECGC 13110402), peaked at around 10 hours for *Lactobacillus fermentum* NCIMB 30226 and peaked at around 16 hours for *Lactobacillus plantarum* 2830 (ECGC 13110402).

GOS Synthesis

Based on the B gal activity studies, GOS was then synthesised in each species/strain by harvesting the cells at the peak activity time point. 50 ml pre-overnight cultures were prepared anaerobically at 37° C. in the modified MRS medium. Overnight cultures in 3 L batches were prepared anaerobic at 37° C. in the modified MRS medium. The cells were harvested at 12 hours for *Lactobacillus plantarum* 2830 (ECGC 13110402), 10 hours *Lactobacillus fermentum* NCIMB 30226 and 16 hours for *Lactobacillus fermentum* ATCC 11976.

The harvested cells were then centrifuged at 10,000 g for 15 minutes. The cells then washed in sodium phosphate buffer (50 mM, pH 6.8) and centrifuged for a further 5 minutes at 10,000 g and then resuspend in 10 ml buffer. The cells were then lysed using liquid nitrogen freeze thaw for 3 cycles and a cell disrupter run at 45000 PSI for 2 passes. The lysate was then centrifuge at 15,000 g for 40 mins and stored at −80° C. prior to further analysis.

Optimisation Analysis

A range of potential optimisation conditions were assessed in each of the three organisms: 1, 2, and 4U of enzyme activity/ml; the growth medium containing 15, 20, 30, 40, 50% lactose; incubation temperatures of 40, 50, 55, 60, 65, 75° C.; and sampling taken at 0, 4, 8, 12, 24, 30 hour intervals. After incubation, the samples were heated at 95°

C. for 5 min to denature enzymes and then filtered and stored at −20° C. prior to further analysis.

The Standards used in this analysis were BiMuno® (a product marketed by Clasado Ltd containing galacto-oligosaccharide), lactose, glucose and galactose. The percentage of sugars were assessed using area under the curve analysis.

Figure 22:
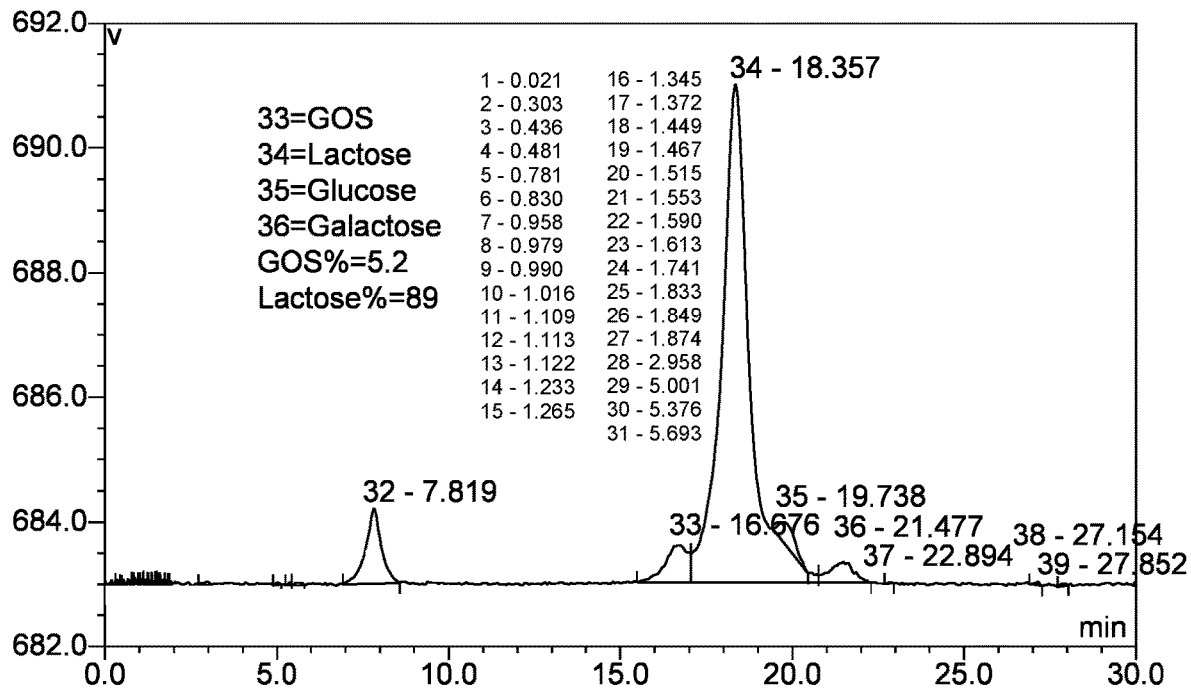
FIG. 22 shows a chromatogram for *Lactobacillus plantarum* 2830 (ECGC 13110402) (GOS %=5.2 and Lactose %=89) used to assess initial GOS production.
Figure 23:
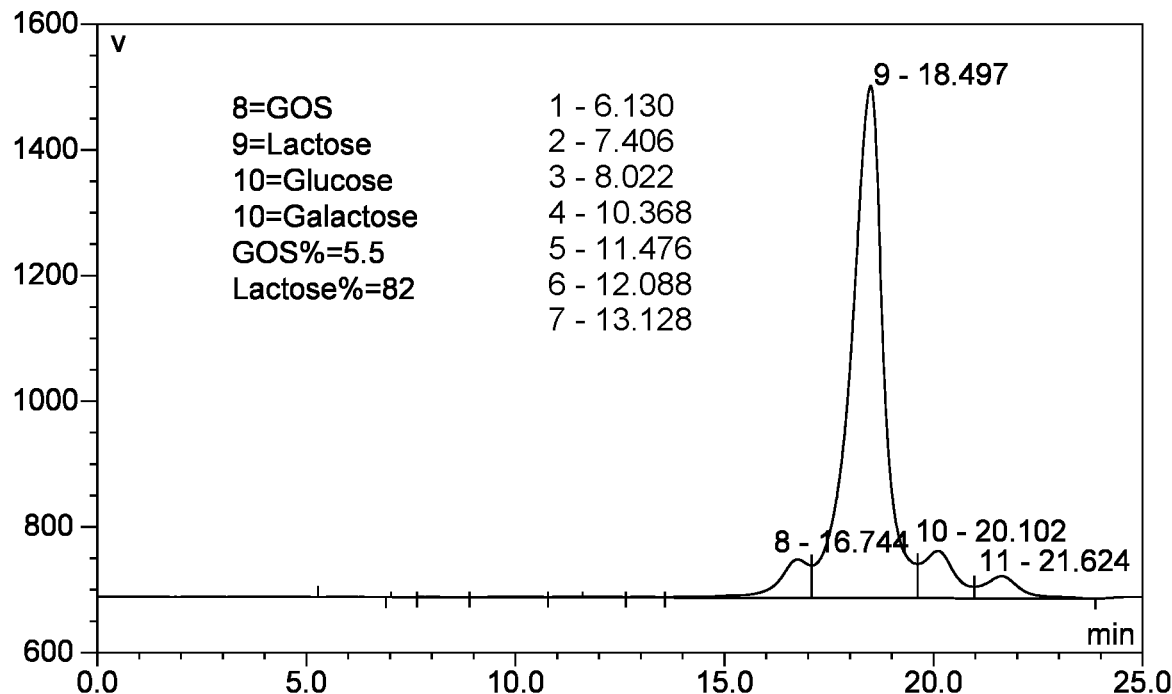
FIG. 23 shows a chromatogram for *Lactobacillus fermentum* NCIMB 30226 (GOS %=5.5 and Lactose %=82) used to assess initial GOS production.
Figure 24:
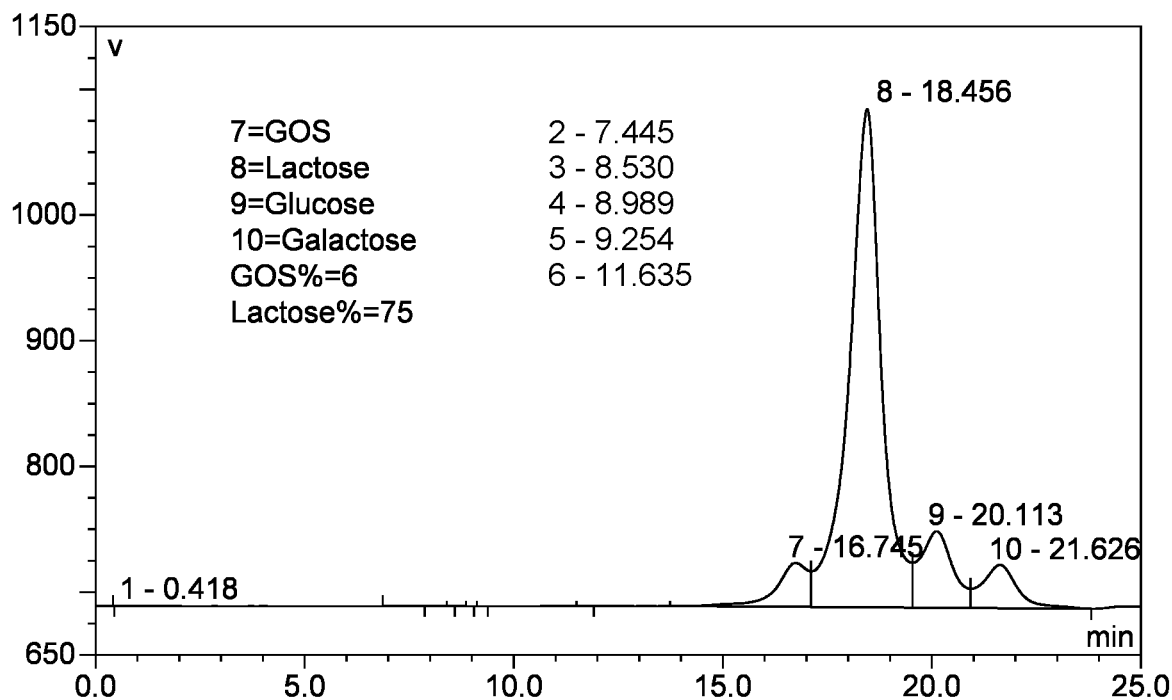
FIG. 24 shows a chromatogram for *Lactobacillus fermentum* ATCC 11976 (GOS %=6 and Lactose %=75) used to assess initial GOS production.
Figure 25:
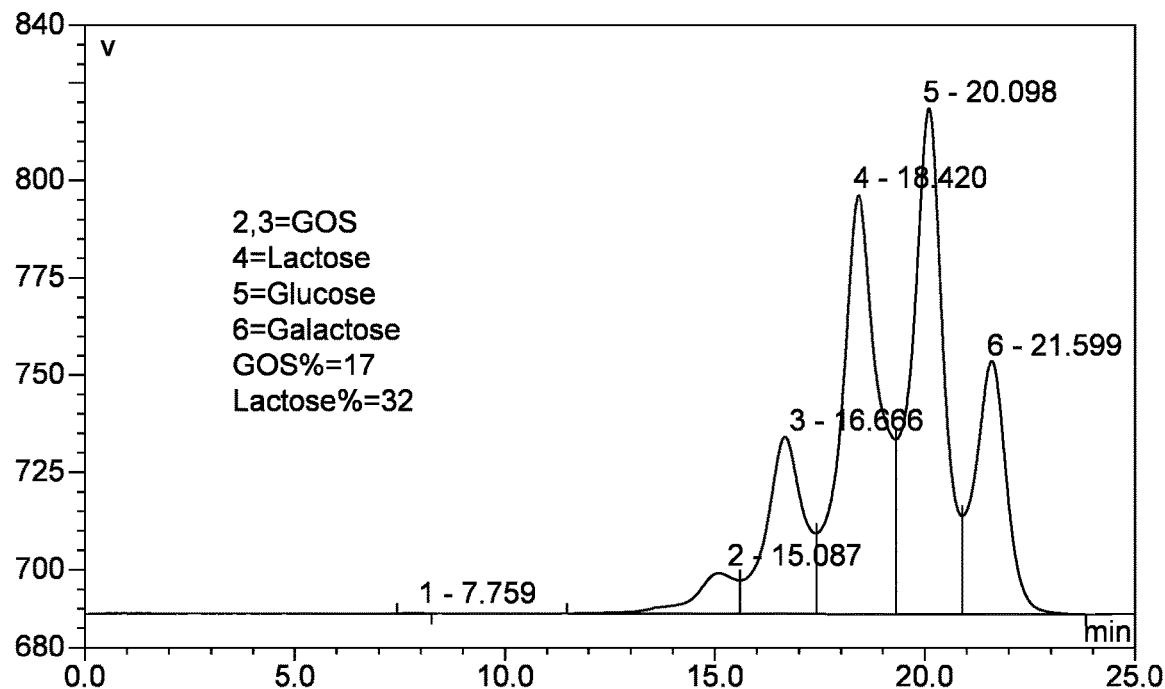
FIG. 25 shows a chromatogram for a control strain of *Lactobacillus delbruecki* (GOS %=17 and Lactose %=32)

No GOS production was established at 60, 65 and 75° C. (although the B gal activity assay has been carried out at these temperatures and did show activity). Generally low GOS yields, below 10% were found and this was likely due to the enzyme not being concentrated and higher levels of water reactions favours hydrolysis. There was evidence of GOS production from *Lactobacillus plantarum* 2830 (ECGC 13110402). FIGS. 22 to 25 shows chromatograms illustrating the evidence of GOS production in the selected organisms and *Lactobacillus delbruecki* as a control in 20% lactose, 2 units of enzyme, grown at 50° C. and sampled at 6 hours. FIG. 22 shows the results for *Lactobacillus plantarum* 2830 (ECGC 13110402) (GOS %=5.2 and Lactose %=89); FIG. 23 shows the results for *Lactobacillus fermentum* NCIMB 30226 (GOS %=5.5 and Lactose %=82); FIG. 24 shows the results *Lactobacillus fermentum* ATCC 11976 (GOS %=6 and Lactose %=75); and FIG. 25 shows the results for a control strain of *Lactobacillus delbruecki* (GOS %=17 and Lactose %=32) to establish that the reaction was working.

Figure 26:
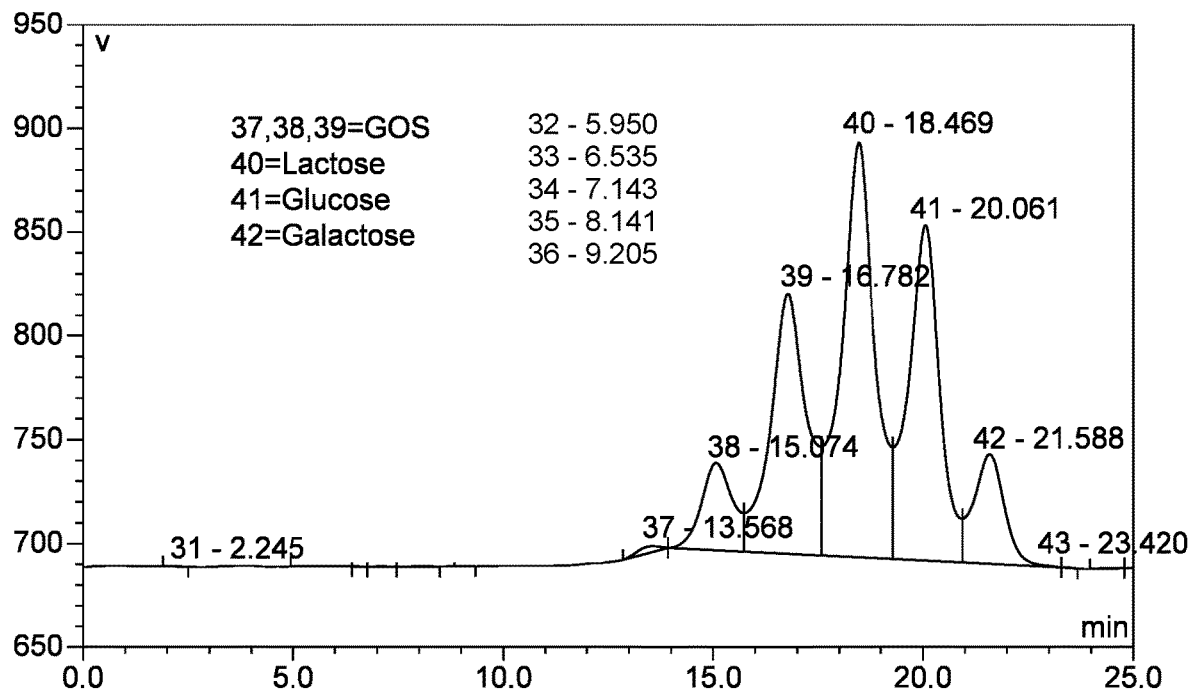
FIG. 26 shows a chromatogram for *Lactobacillus plantarum* 2830 (ECGC 13110402) at 14 hours grown in 40% lactose at 50° C. with 6 units enzyme/ml.
Figure 27:
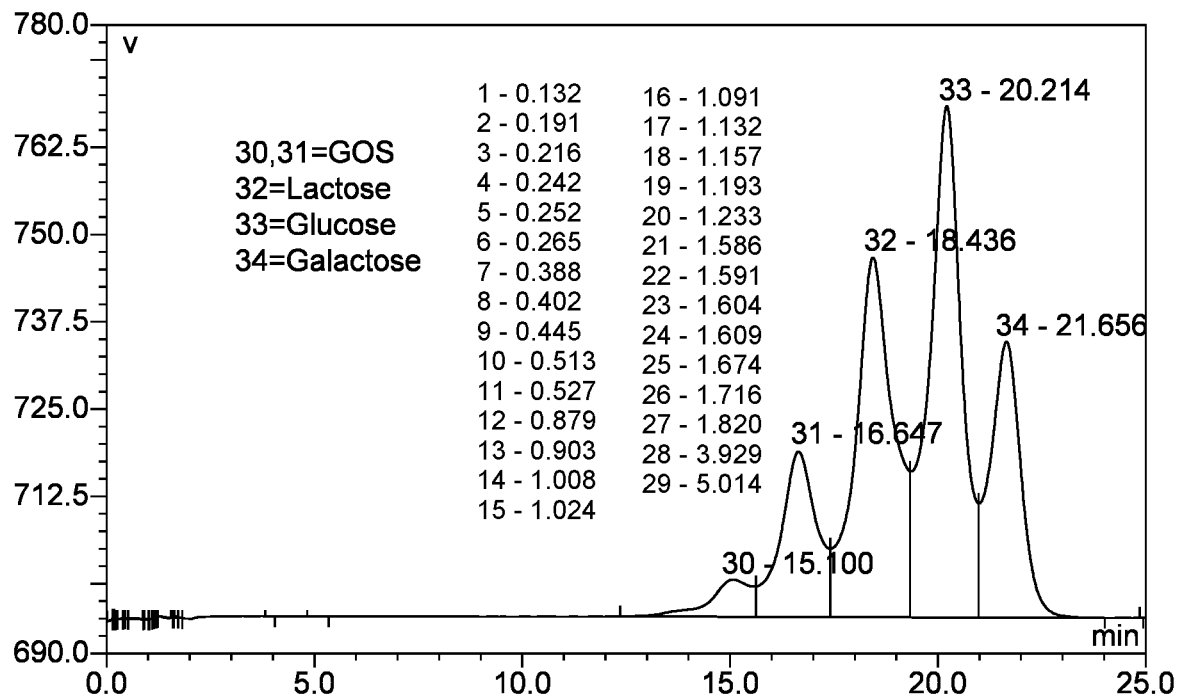
FIG. 27 shows a chromatogram for *Lactobacillus plantarum* 2830 (ECGC 13110402) at 24 hours grown in 40% lactose at 50° C. with 6 units enzyme/ml.
Figure 28:
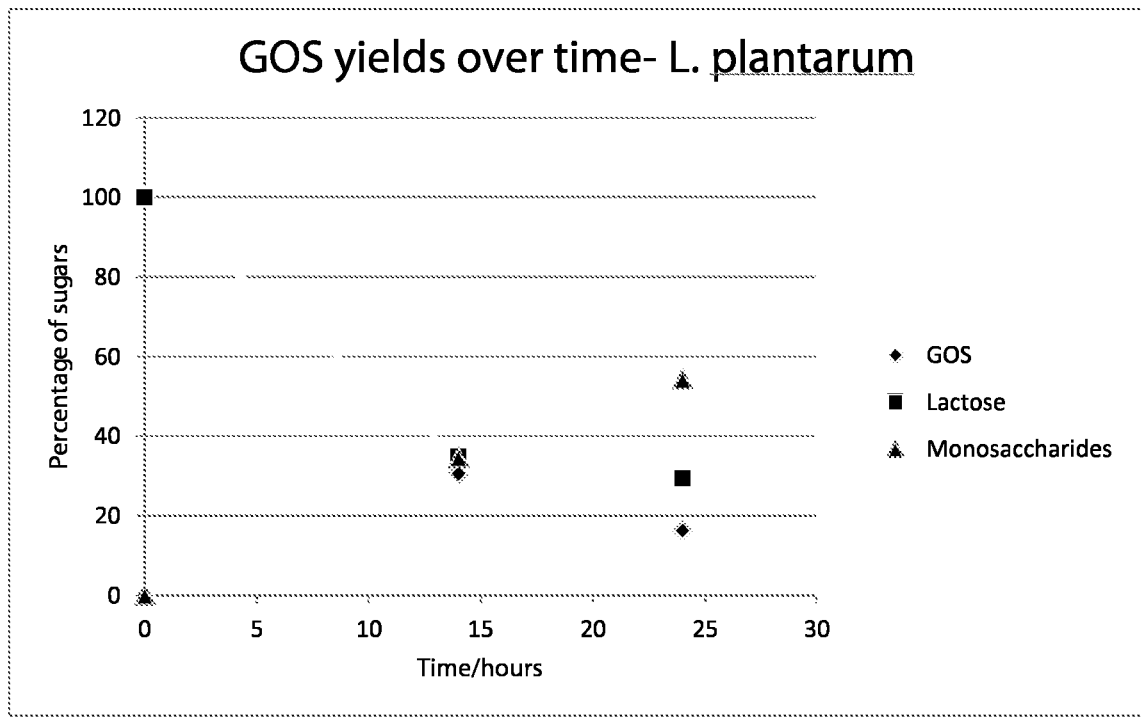
FIG. 28 shows a graph of the yield of GOS, lactose and monosaccharides at 12 and 24 hours for *Lactobacillus plantarum* 2830 (ECGC 13110402)

Further synthesis reactions using *B. bifidum* as a control were undertaken. *B. bifidum* crude cell extracts were used to synthesize a GOS product similar to Bimuno® to assess whether the assay was working properly. Growth of the selected organisms was on 40% lactose at 50° C. and 6 units enzyme/ml. A plating out protocol was used to provide pure cultures after pre overnight and before harvesting the resultant 3 L cultures. FIG. 26 shows a chromatogram for *Lactobacillus plantarum* 2830 (ECGC 13110402) at 14 hours, whereas FIG. 27 shows a chromatogram for *Lactobacillus plantarum* 2830 (ECGC 13110402) at 24 hours. FIG. 28 shows a graph of the yield of GOS, lactose and monosaccharides at 12 and 24 hours for *Lactobacillus plantarum* 2830 (ECGC 13110402) and the results are also shows in Table 9 below:

TABLE 9

| Time | GOS % | Lactose % | Monosaccharides % |
|---|---|---|---|
| 0 | 0 | 100 | 0 |
| 14 | 30.49831 | 34.84451 | 34.65717 |
| 24 | 16.30435 | 29.34783 | 54.34783 |

The results show that a transgalactosylation reaction is occurring and that lactose (substrate) is being depleted and monosaccharides (products) are increasing. GOS is synthesised by B gal but then after time is hydrolysed by B gal. From an optimisation point of view, it was established that 30.5% max GOS at 66% Lactose conversion at 14 hr was preferred.

Figure 29:
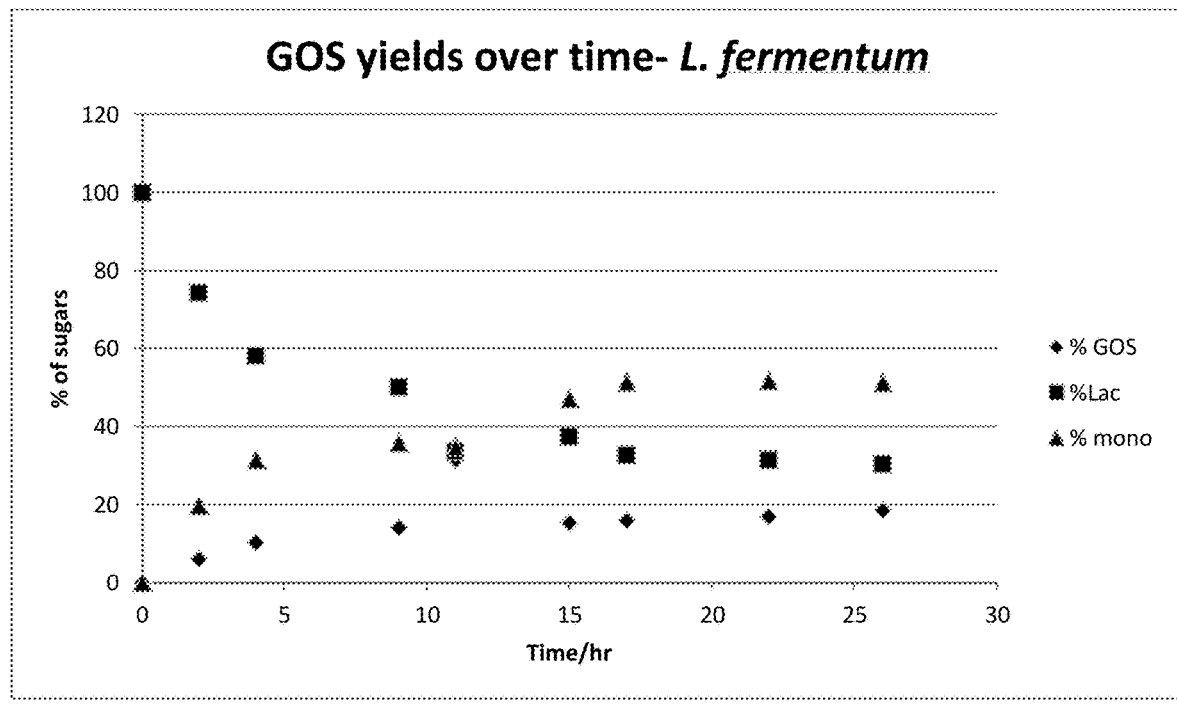
FIG. 29 is a graph showing the percentage of sugars for *Lactobacillus fermentum* NCIMB 30226 over 24 hr gown in 40% lactose at 50° C.

The optimised GOS production in *Lactobacillus plantarum* 2830 (ECGC 13110402) may be similar to two other strains, *Lactobacillus plantarum* 2691 (ECGC 13110401) and *Lactobacillus plantarum* 2828 (ECGC 13110403) and other strains of *Lactobacillus plantarum* which have been under investigation for the control of cholesterol, heart disease, diabetes or obesity:

Similar experiments were conducted for both Synthesis reactions for both *Lactobacillus fermentum* NCIMB 30226 and *Lactobacillus fermentum* ATCC 11976. The data varies as enzyme units were not being controlled. FIG. 29 is a graph showing the percentage of sugars for *Lactobacillus fermentum* NCIMB 30226 over 24 hr gown in 40% lactose at 50° C. and also shown in greater detail in the Table 10 below:

TABLE 10

| Time | % GOS | % Lac | % mono |
|---|---|---|---|
| 0 | 0 | 100 | 0 |
| 2 | 5.940594 | 74.25743 | 19.80198 |
| 4 | 10.36036 | 58.10811 | 31.53153 |
| 9 | 14.0625 | 50 | 35.9375 |
| 11 | 31.64557 | 33.5443 | 34.81013 |
| 15 | 15.46943 | 37.42065 | 47.10992 |
| 17 | 15.88785 | 32.71028 | 51.40187 |
| 22 | 16.90821 | 31.40097 | 51.69082 |
| 26 | 18.44262 | 30.32787 | 51.22951 |

The results show that a clear transgalactosylation reaction is occurring and an optimum 31% GOS yield at 66.5% lactose conversion at 12 hr was established.

Figure 30:
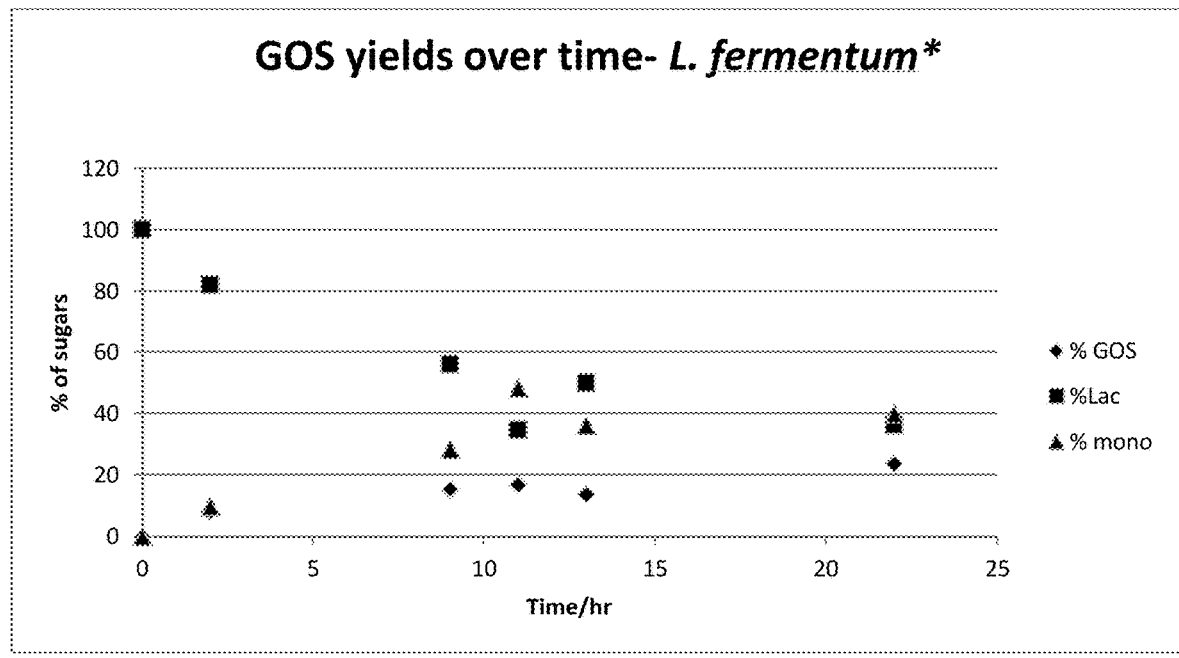
FIG. 30 is a graph showing the percentage of sugars for *Lactobacillus fermentum* ATCC 11976 over 24 hr 40% lactose at 50° C.

The results for the percentage of sugars for *Lactobacillus fermentum* ATCC 11976 over 24 hr 40% lactose at 50° C. is show in FIG. 30 and also in the Table 11 below:

TABLE 11

| Time | % GOS | % Lac | % mono |
|---|---|---|---|
| 0 | 0 | 100 | 0 |
| 2 | 8.252427 | 82.03883 | 9.708738 |
| 9 | 15.44715 | 56.09756 | 28.45528 |
| 11 | 16.90141 | 34.64789 | 48.4507 |
| 13 | 13.80952 | 50 | 36.19048 |
| 22 | 23.72881 | 36.27119 | 40 |

The results show that GOS is being produced and an optimum 23% GOS yield at 64% lactose conversion at 22 hours was established.

FIGS. 31A and 31B shows the comparatively different percentage of sugars (and GOS yield) between the *Lactobacillus fermentum* NCIMB 30226 and *Lactobacillus fermentum* ATCC 11976 strains when grown in 15% lactose at 40° C. and both show similar yields of GOS at similar time points. The results also demonstrate that little transgalactosylation is expected due to the low lactose concentration (15%). The reaction was carried out to ensure the enzyme was active which it was (hydrolysis) and also showed high monosaccharide production under these conditions.

FIGS. 32A and 32B shows the comparatively different percentage of sugars (and GOS yield) between the *Lactobacillus fermentum* NCIMB 30226 and *Lactobacillus fermentum* ATCC 11976 strains when grown in 40% lactose at 40° C. *Lactobacillus fermentum* NCIMB 30226 showed a peak (51.08%) in GOS production at 18 hours which tailed off quickly thereafter. *Lactobacillus fermentum* ATCC 11976 showed a peak (40.47%) in GOS production at 2 hours and retained relatively high % of GOS (between 26 to 34%) for sometime thereafter.

The forgoing embodiments are not intended to limit the scope of the protection afforded by the claims, but rather to describe examples of how the invention may be put into practice.

Biological Deposits

The application refers to and claims the following indication of deposited biological material:
  Name: European Collection of Cell Cultures
  Address: Public Health England Culture Collections
Porton Down
Salisbury
SP4 0JG
United Kingdom
Date: 4 Nov. 2013
Accession Number: 13110401
—and—
Name: European Collection of Cell Cultures
Address: Public Health England
Culture Collections
Porton Down
Salisbury
SP4 0JG
United Kingdom
Date: 4 Nov. 2013
Accession Number: 13110402
—and—
Name: European Collection of Cell Cultures
Address: Public Health England
Culture Collections
Porton Down
Salisbury
SP4 0JG
United Kingdom
Date: 4 Nov. 2013
Accession Number: 13110403

The invention claimed is:

1. A *Lactobacillus* synbiotic composition comprising *Lactobacillus plantarum* 2830 deposited at the European Collection of Cell Cultures (ECGC) under Accession Number 13110402 and galacto oligosaccharide (GOS) produced by *Lactobacillus plantarum* 2830 ECGC 13110402, wherein the GOS acts as a selective growth medium for *Lactobacillus plantarum* 2830 ECGC 13110402, and wherein the GOS is produced by reverse β-galactosidase reaction in *Lactobacillus plantarum* 2830 ECGC 13110402, and wherein at least one of:
 (a) the composition is encapsulated;
 (b) the composition further comprises an excipient or carrier compound;
 (c) the composition is in the form of a drinkable liquid or solid or liquid foodstuff;
 (d) the composition further comprises an additional active ingredient; and
 (e) the *Lactobacillus plantarum* 2830 ECGC 13110402 is freeze-dried.

2. The composition as claimed in claim 1 for use as a medicament.

3. The composition as claimed in claim 1 for use as a dietary supplement.

4. The composition as claimed in claim 1 for use in the management of cholesterol or in the treatment of high cholesterol.

5. The composition as claimed claim 1 for use in the management or treatment of a metabolic syndrome.

6. The composition as claimed in claim 1 for use in weight management.

7. The composition as claimed in claim 1 for use in the management or treatment of diabetes.

* * * * *